(12) United States Patent
Sauer

(10) Patent No.: US 12,070,206 B2
(45) Date of Patent: Aug. 27, 2024

(54) MINIMALLY INVASIVE SUTURING DEVICE

(71) Applicant: LSI Solutions, Inc., Victor, NY (US)

(72) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 0 days.

(21) Appl. No.: 17/743,225

(22) Filed: May 12, 2022

(65) Prior Publication Data

US 2022/0346771 A1 Nov. 3, 2022

Related U.S. Application Data

(63) Continuation of application No. 16/259,794, filed on Jan. 28, 2019, now Pat. No. 11,357,498.

(60) Provisional application No. 62/622,959, filed on Jan. 28, 2018.

(51) Int. Cl.
*A61B 17/04* (2006.01)
*A61B 17/062* (2006.01)
*A61B 17/00* (2006.01)

(52) U.S. Cl.
CPC ...... *A61B 17/0469* (2013.01); *A61B 17/0482* (2013.01); *A61B 17/0625* (2013.01); *A61B 2017/00243* (2013.01); *A61B 2017/00314* (2013.01); *A61B 2017/00323* (2013.01); *A61B 2017/0472* (2013.01)

(58) Field of Classification Search
CPC ........ A61B 17/0469; A61B 2017/0472; A61B 2017/00314; A61B 2017/00323
See application file for complete search history.

(56) References Cited

U.S. PATENT DOCUMENTS

| | | | |
|---|---|---|---|
| 2009/0312773 A1 | 12/2009 | Cabrera et al. | |
| 2012/0232567 A1* | 9/2012 | Fairneny | A61B 17/0482 606/147 |
| 2014/0135685 A1* | 5/2014 | Kabe | A61F 2/246 604/95.04 |

OTHER PUBLICATIONS

International Search Report and Written Opinion mailed Apr. 11, 2019, for PCT/US2019/015444, filed Jan. 28, 2019.

* cited by examiner

*Primary Examiner* — Ryan J. Severson
(74) *Attorney, Agent, or Firm* — Michael E. Coyne

(57) ABSTRACT

A minimally invasive suturing device is disclosed. The minimally invasive suturing device has a shaft and a distal tip. The minimally invasive suturing device also has a flexible span coupling the distal tip to the shaft. The flexible span has an angling link, a plurality of bending links, and an end link.

12 Claims, 27 Drawing Sheets

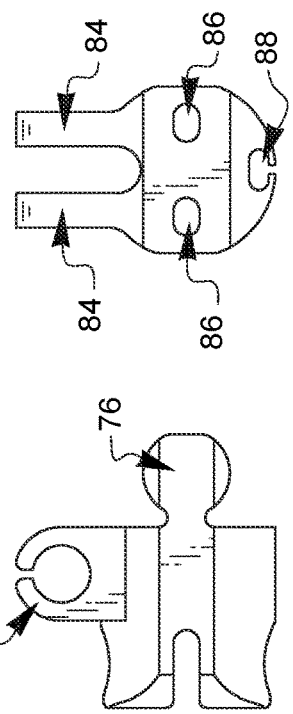

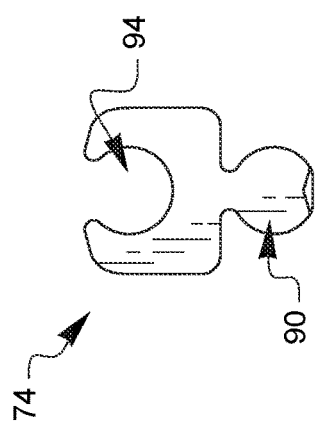
FIG. 5E
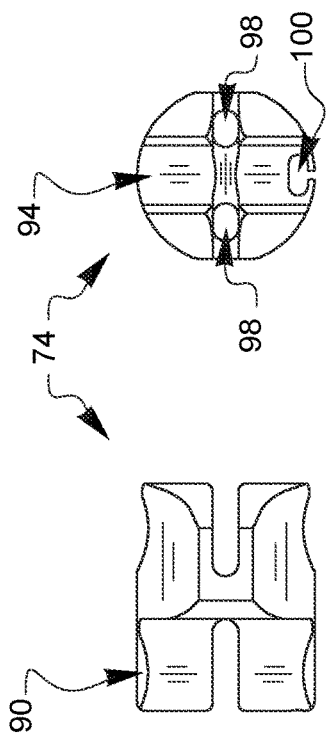
FIG. 5D
FIG. 5C
FIG. 5A
FIG. 5B
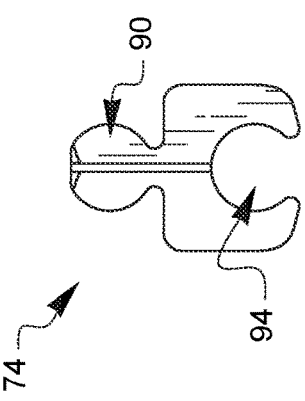
FIG. 5F
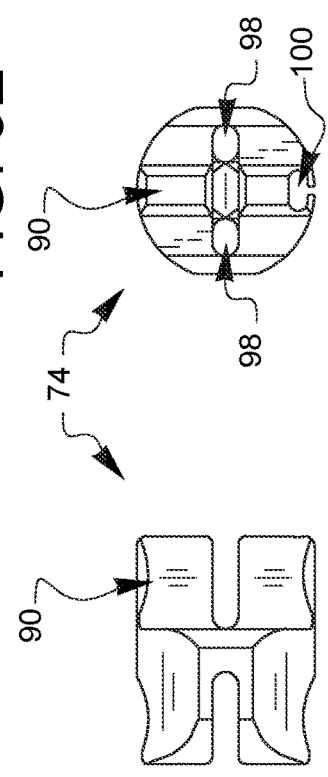

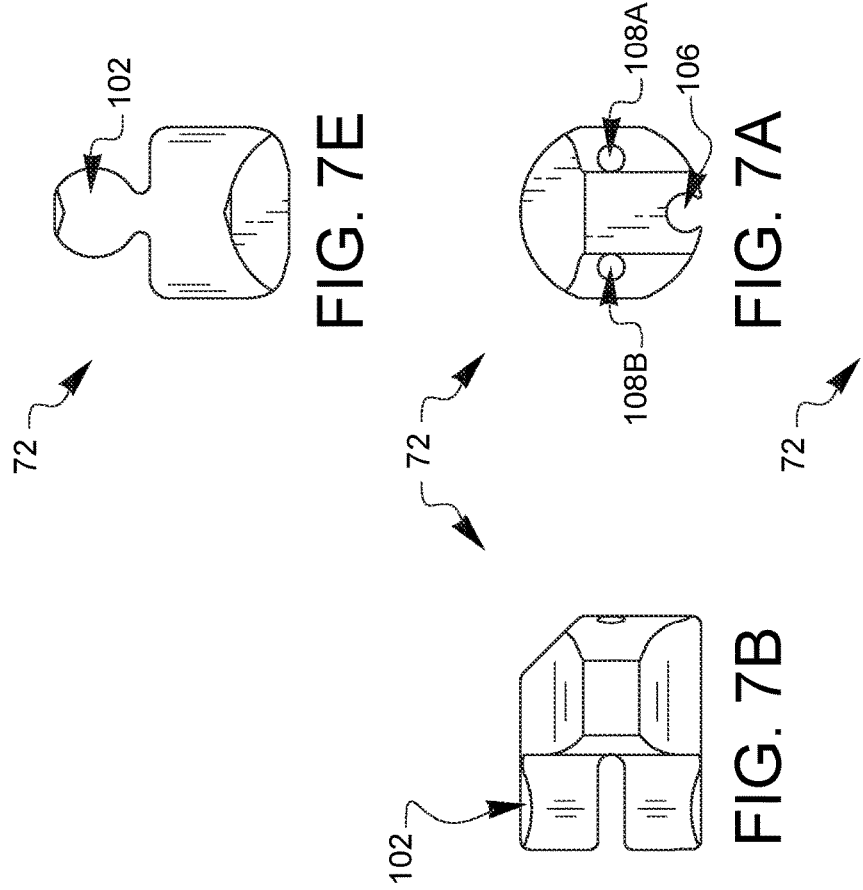

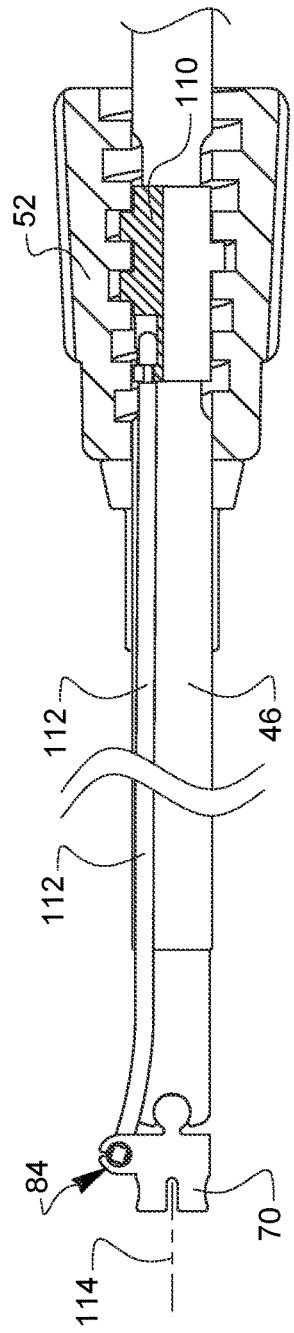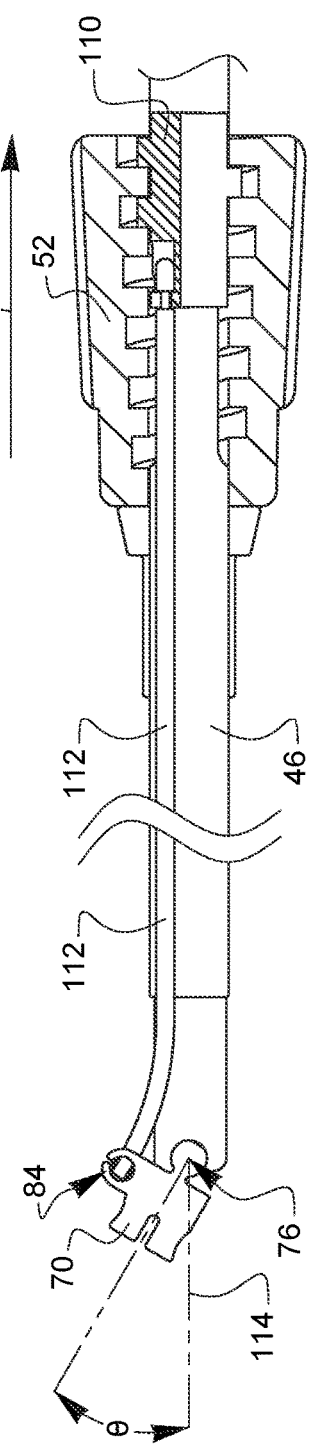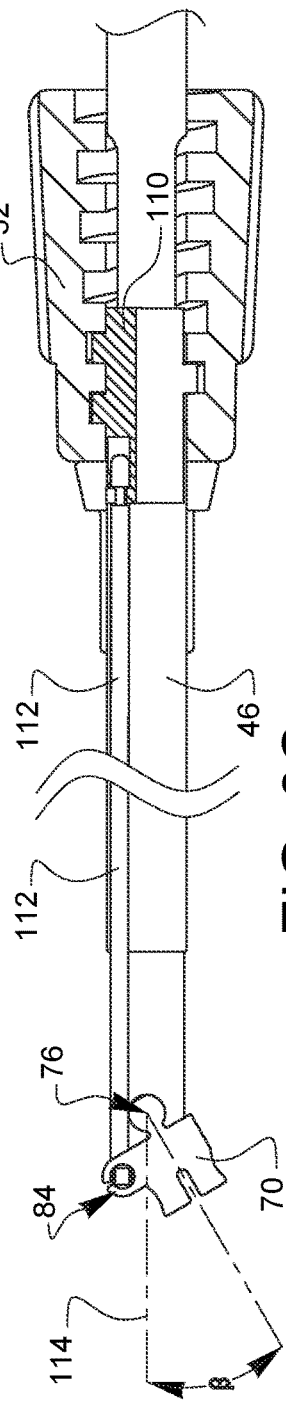

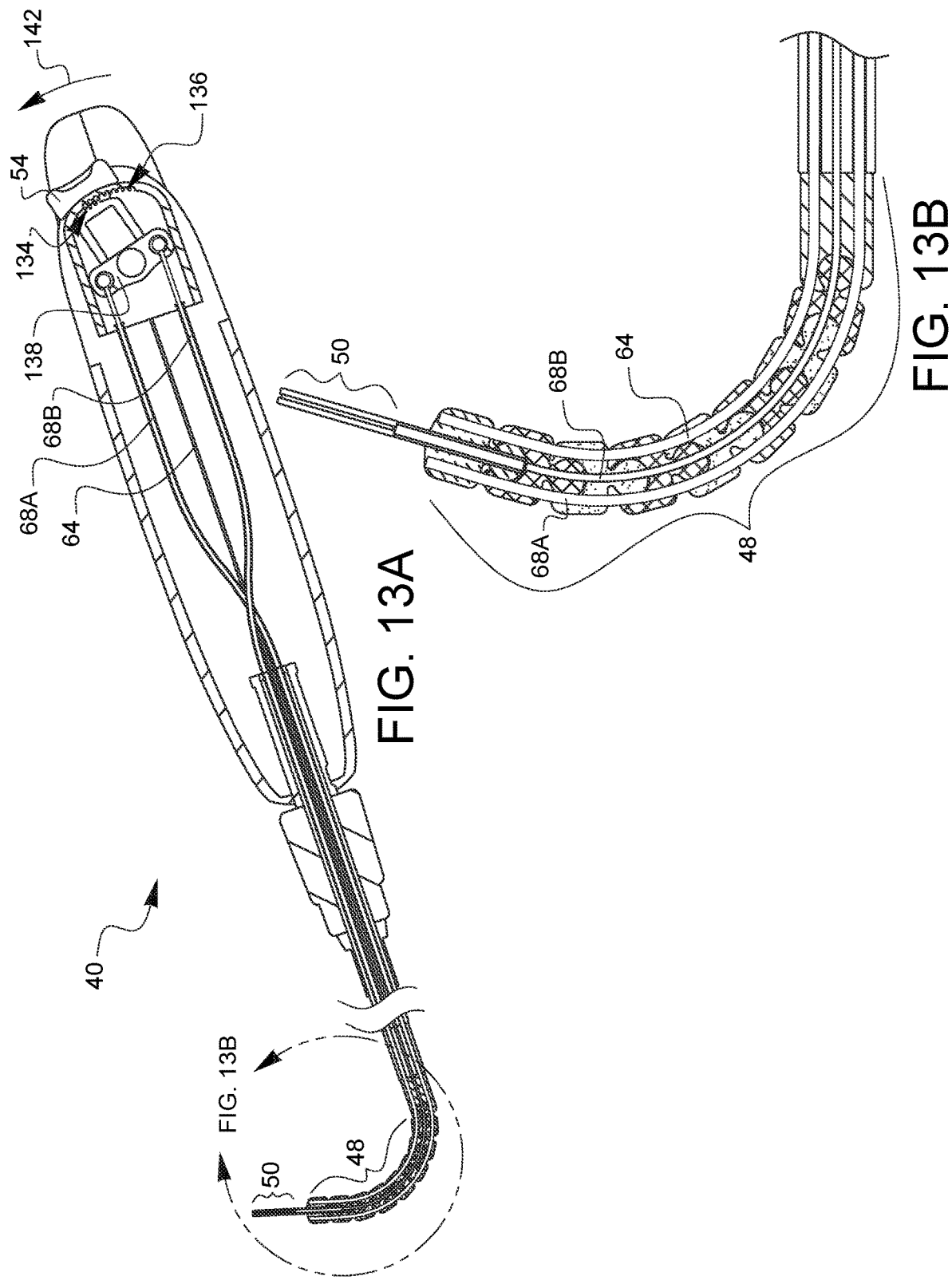

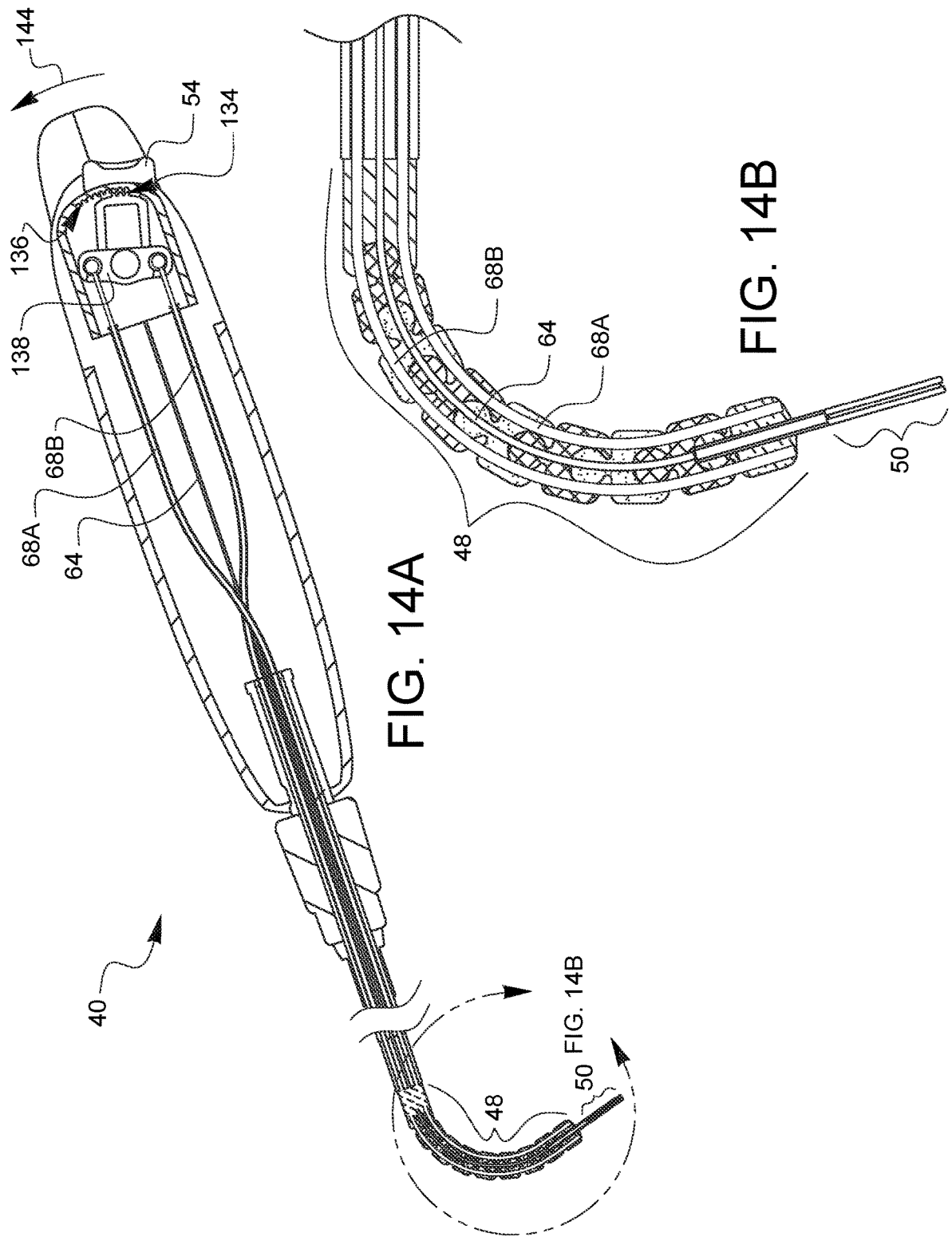

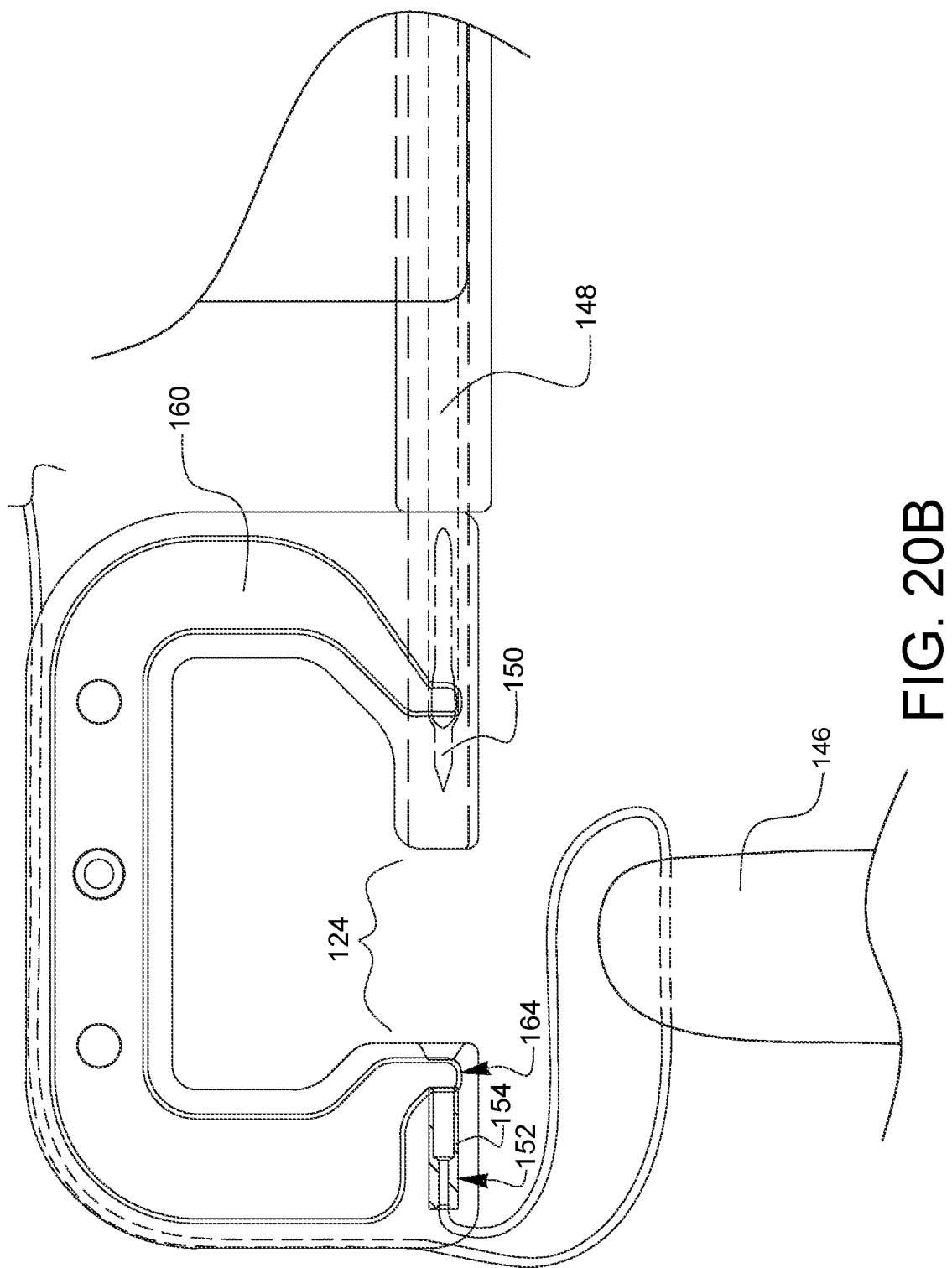

MINIMALLY INVASIVE SUTURING DEVICE

RELATED APPLICATION

This application is a continuation of U.S. patent application Ser. No. 16/259,794, filed Jan. 28, 2019, which claims priority to U.S. Provisional Patent Application 62/622,959, filed Jan. 28, 2018, each of which is hereby incorporated by reference in its entirety.

FIELD

The claimed invention relates to surgical devices, and more specifically to minimally invasive surgical devices.

SUMMARY

A minimally invasive suturing device is disclosed. The minimally invasive suturing device has a shaft and a distal tip. The minimally invasive suturing device also has a flexible span coupling the distal tip to the shaft. The flexible span has an angling link, a plurality of bending links, and an end link.

BACKGROUND

Great advances have been made in cardiac surgery with regard to performing more and more procedures using minimally invasive approaches. For example, aortic valve replacement, mitral valve replacement, and mitral valve repair are routinely performed using minimally invasive approaches. Unfortunately, coronary artery bypass is one area of cardiac surgery which is not yet routinely done using minimally invasive approaches. One of the limiting factors for a minimally invasive cardiac surgical approach to coronary artery bypass surgery appears to be an inability to maneuver an automated surgical suturing device properly through a small access hole for all of the different positions which would be necessary when forming an anastomosis for such surgery. Therefore, it would be desirable to have an economical and reliable minimally invasive suturing device which is highly maneuverable when used through a small access opening while still being able to create a running stitch for an anastomosis.

BRIEF DESCRIPTION OF THE DRAWINGS

FIGS. 3A, 3B, 3C, 3D, 3E, and 3F are distal, right, left, proximal, top, and bottom elevational views, respectively, of the angling link of FIGS. 2A, 2B.

FIGS. 5A, 5B, 5C, 5D, 5E, and 5F are proximal, left, right, distal, top, and bottom views, respectively, of the bending link of FIGS. 4A, 4B.

FIGS. 7A, 7B, 7C, 7D, 7E, and 7F are distal, right, left, proximal, top, and bottom elevational views, respectively, of the end link of FIGS. 6A, 6B.

FIGS. 8A-8C schematically illustrate how an angler knob is used to adjust a first angle of a flexible span with respect to the device shaft.

FIGS. 12A, 13A, and 14A are cross-sectioned top schematic views of the minimally invasive suturing device for explaining how an articulation control is used to adjust an articulation angle (a second, separate angle from that discussed with respect to FIGS. 8A-8C).

FIG. 13B is an enlarged view of the flexible span from FIG. 13A.

FIG. 14B is an enlarged view of the flexible span from FIG. 14A.

Figure 1A:
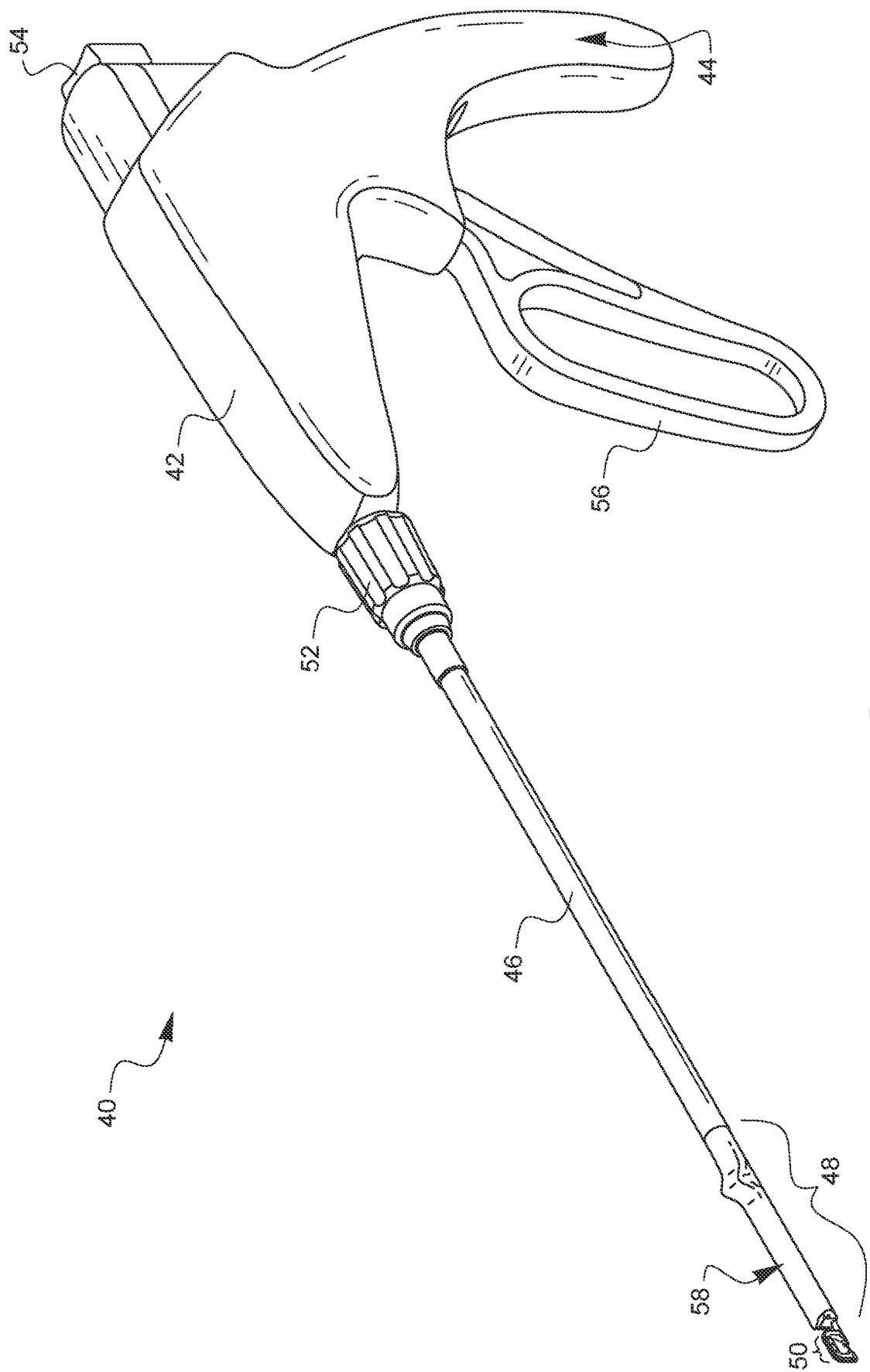
FIG. 1A is a perspective view of one embodiment of a minimally invasive suturing device.

It will be appreciated that for purposes of clarity and where deemed appropriate, reference numerals have been repeated in the figures to indicate corresponding features, and that the various elements in the drawings have not necessarily been drawn to scale in order to better show the features.

DETAILED DESCRIPTION

FIG. 1A is a perspective view of one embodiment of a minimally invasive suturing device 40. The device 40 has a housing 42 which also forms a handle 44. A shaft 46 extends from the housing 42. The shaft 46 has a flexible span 48 at the distal end of the shaft 46. The flexible span 48 couples a distal tip 50 to the shaft 46. An angler knob 52 is located on the shaft 46 near the housing 42. The angler knob 52 is configured to manipulate one part of the flexible span 48 to move the distal tip 50 in a first plane. An articulation control 54 is located on the housing 42 and is configured to manipulate another part of the flexible span 48 to move the distal tip 50 in a second plane. A lever 56 protrudes from the housing and may be squeezed towards the handle 44 to cause a needle (not visible in this view) to suture tissue when placed within an opening of the distal tip 50.

Figure 1B:
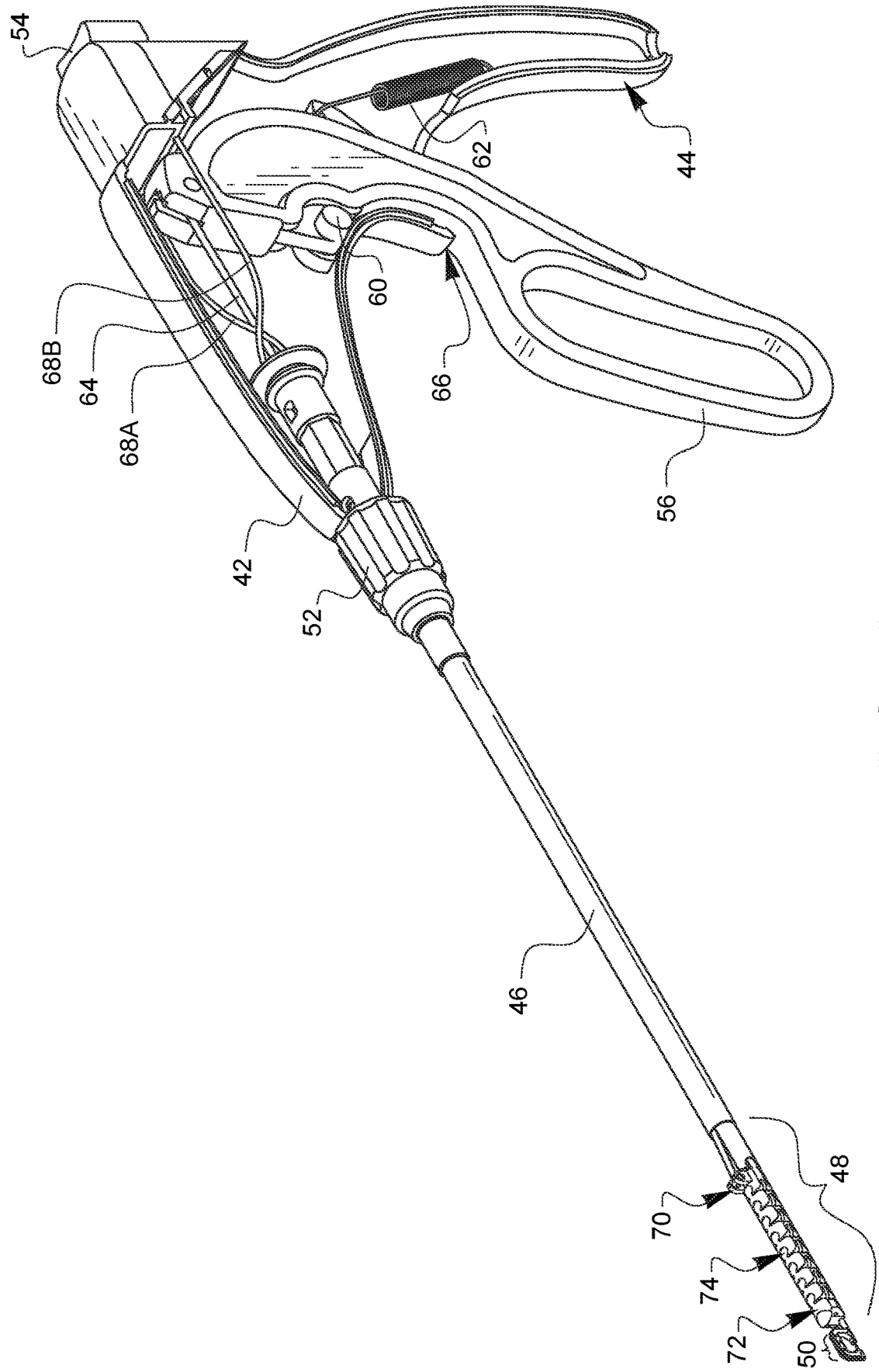
FIG. 1B is a perspective view of the minimally invasive surgical suturing device from FIG. 1A with a portion of the housing removed.

FIG. 1B is a perspective view of the minimally invasive surgical suturing device 40 from FIG. 1A with a portion of the housing 42 removed and a flexible cover 58 (visible in FIG. 1A) removed from the flexible span 48. In FIG. 1B, it can be seen that the lever 56 is pivotable about a pivot point 60. A spring 62 is coupled between the housing 42 and the lever 56 to bias the lever 56 against the housing 42 as shown in FIG. 1B. A needle drive wire 64 is coupled to the top end of the lever 56 and extends down through the shaft 46, through the flexible span 48, and ending in a needle tip (not visible in this view) within the distal tip 50. When the lever 56 is squeezed towards the handle 44, the lever pivots around pivot point 60, moving the needle drive wire 64 distally towards the distal tip 50. When the lever 56 is released, spring 62 causes the lever 56 to pivot back to where it contacts the housing 42 at location 66, thereby pulling the needle drive wire 64 in a proximal direction, away from the distal tip 50. The location 66 on the housing 42 may be made from a flexible material such that the lever 56 may be hyperextended by the user farther away from the handle 44 than is shown in FIG. 1B. This hyperextension has utility which will be discussed later in this specification.

Portions of first and second articulation cables 68A, 68B are also visible in FIG. 1B. As will be discussed later in this specification, the first and second articulation cables extend from the articulation control 54 to the flexible span 48. The flexible span 48 is made from three types of links. It has an angling link 70 on the side of the flexible span 48 closest to the shaft 46. It also has an end link 72 on the side of the flexible span 48 closest to the distal tip 50. In between the angling link 70 and the end link 72 are a plurality of bending links 74.

Figure 2A:
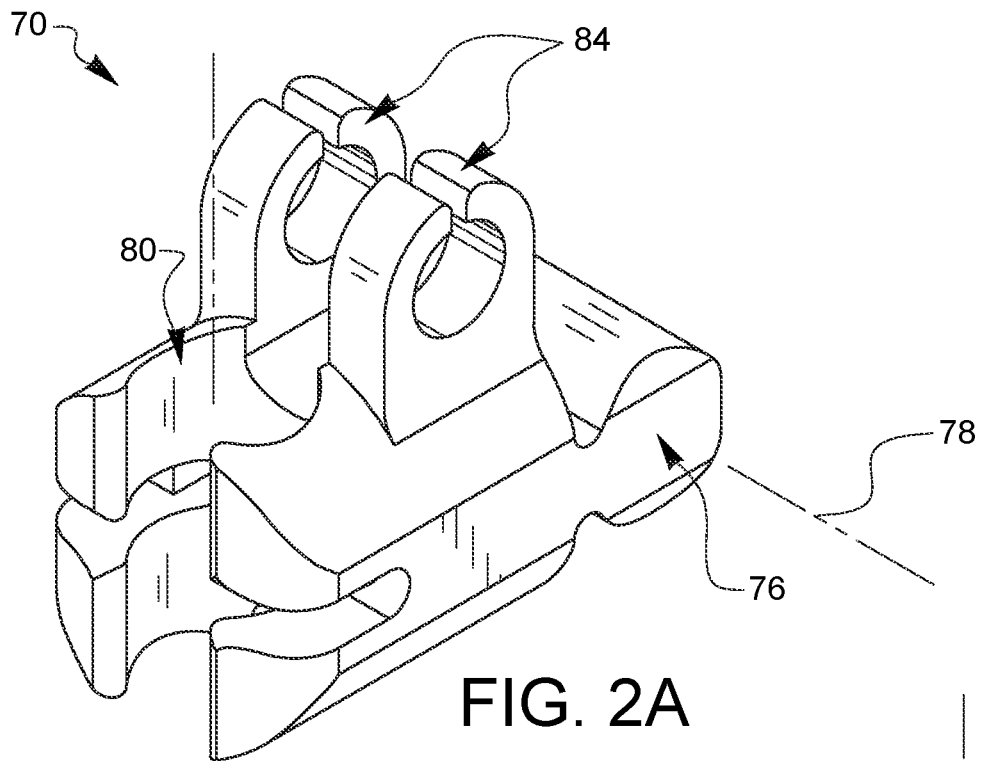
FIGS. 2A and 2B are a distal, top perspective view and a proximal, top perspective view, respectively, of one embodiment of an angling link.
Figure 2B:
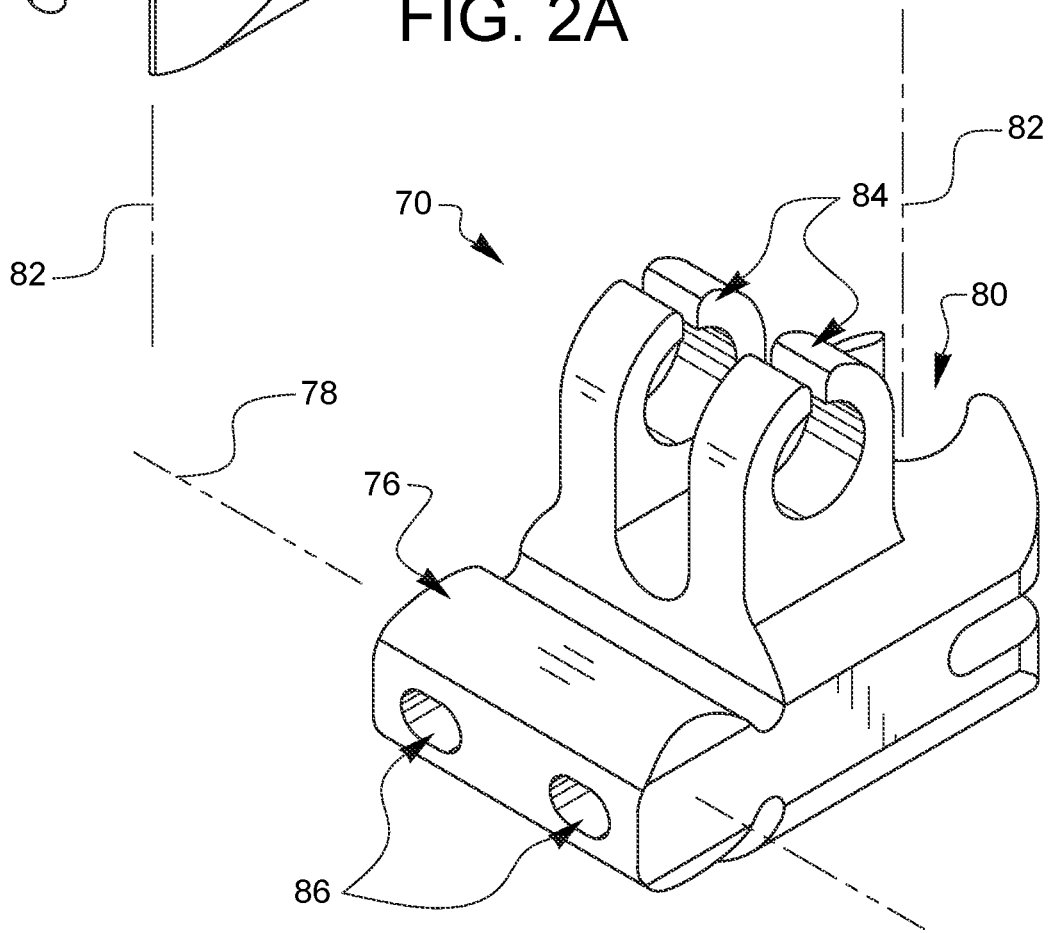

FIGS. 2A and 2B are a distal, top perspective view and a proximal, top perspective view, respectively, of one embodiment of an angling link 70. The proximal end of the angling link 70 has an angling hinge pin 76 which defines an angling pivot axis 78. The angling hinge pin 76 can be pivotably coupled to the shaft 46. The distal end of the angling link 70 defines an articulation socket 80 which has a bending axis 82. The articulation socket 80 of the angling link 70 is configured to mate with an articulation hinge pin from a bending link 74, the features of which will be discussed below. A first plane created by the rotation of a first line, orthogonal to the angling pivot axis 78, about the angling pivot axis 78 is substantially orthogonal to a second plane created by the rotation of a second line, orthogonal to the bending axis 82, about the bending axis 82. The angling link 70 also has an angler drive wire receiver 84 configured to be coupled to an angler driver wire, the features of which will be discussed below. The angling link 70 further has articulation cable channels 86, one for each of the first and second articulation cables 68A, 68B to pass through.

FIGS. 3A, 3B, 3C, 3D, 3E, and 3F are distal, right, left, proximal, top, and bottom elevational views, respectively, of the angling link 70. The distal view of FIG. 3A and proximal view of FIG. 3D show a needle drive wire channel 88 which passes through the bottom of the angling link 70. In this embodiment, both the needle drive wire channel 88 and the articulation cable channels 86 are slotted to accommodate bending of the needle drive wire and/or the articulation cables.

Figure 4A:
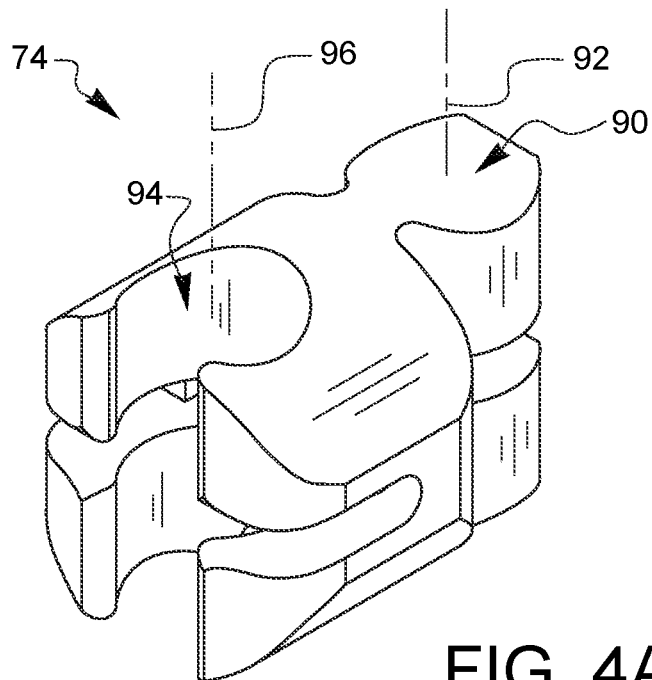
FIGS. 4A and 4B are a distal, top perspective view and a proximal, top perspective view, respectively, of one embodiment of a bending link.
Figure 4B:
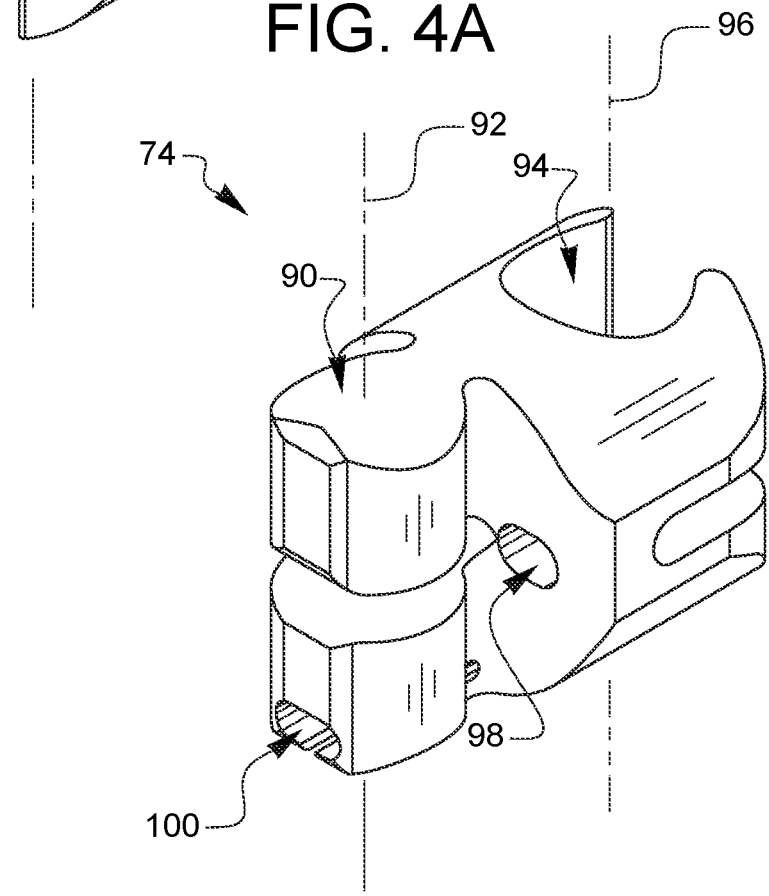

FIGS. 4A and 4B are a distal, top perspective view and a proximal, top perspective view, respectively, of one embodiment of a bending link 74. The proximal end of the bending link 74 has a bending hinge pin 90 which defines a bending axis 92. The distal end of the bending link 74 defines a bending socket 94 which has a bending axis 96. The bending axes 92, 96 are substantially parallel to each other. The bending hinge pin 90 of the bending link 74 may be pivotably coupled to the articulation socket 80 of an angling link or it may be coupled to the bending socket 94 of another bending link 74.

FIGS. 5A, 5B, 5C, 5D, 5E, and 5F are proximal, left, right, distal, top, and bottom views, respectively, of the bending link 74. The proximal view of FIG. 5A and the distal view of FIG. 5D show articulation cable channels 98 and a needle drive wire channel 100 which pass through the bending link 74. In this embodiment, both the needle drive wire channel 100 and the articulation cable channels 98 are slotted to accommodate bending of the needle drive wire and/or the articulation cables.

Figure 6A:
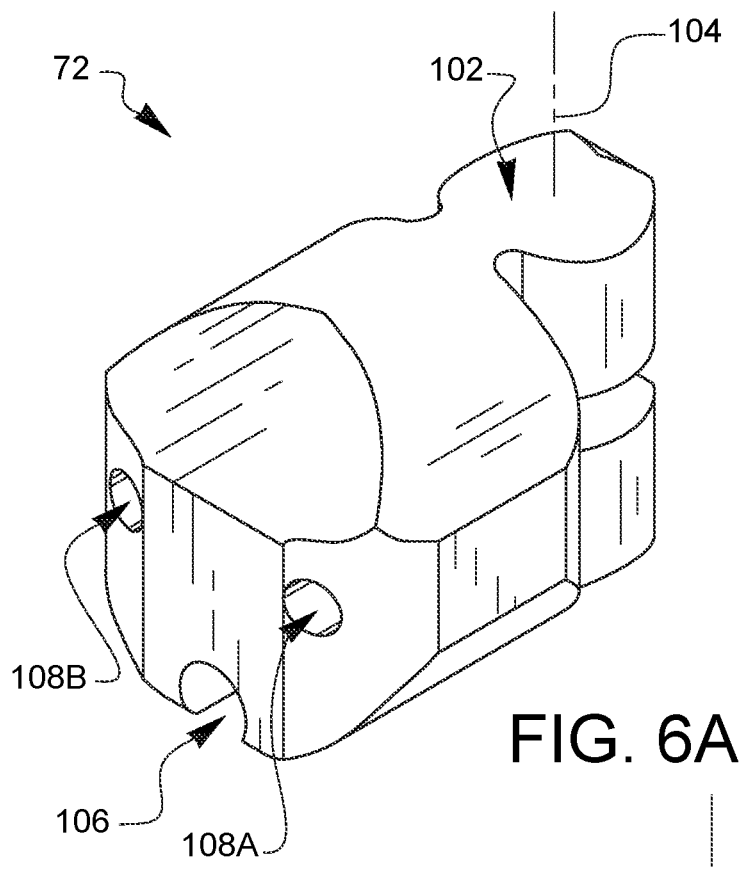
FIGS. 6A and 6B are a distal, top perspective view and a proximal, top perspective view, respectively, of one embodiment of an end link.
Figure 6B:
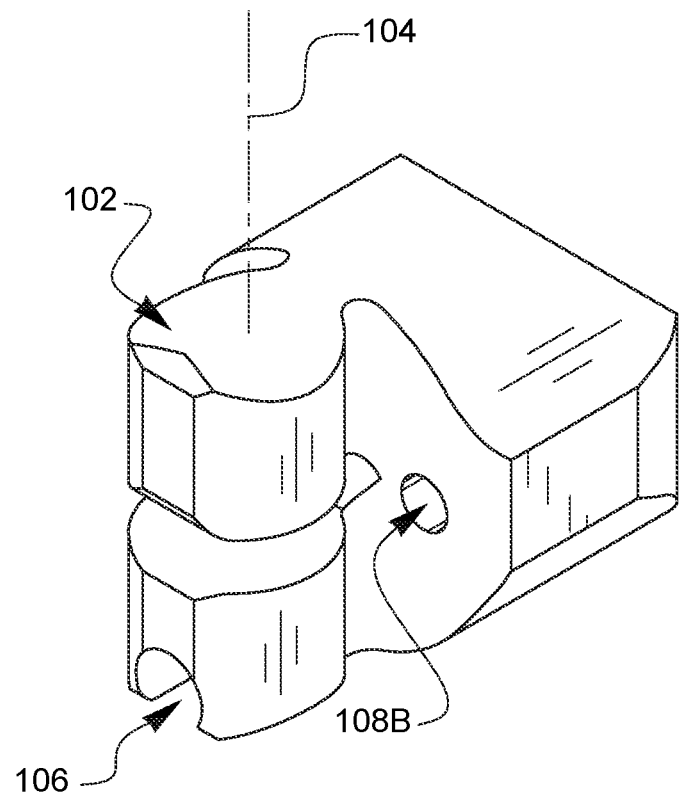

FIGS. 6A and 6B are a distal, top perspective view and a proximal, top perspective view, respectively, of one embodiment of an end link 72. The proximal end of the end link 72 has a bending hinge pin 102 which defines a bending axis 104. The bending hinge pin 102 of the end link 72 may be pivotably coupled to the bending socket 94 of a bending link 74. A tube receiving slot 106 passes through the bottom of the end link 74. The tube receiving slot 74 may be coupled to a needle tube (not shown) through which a needle may traverse. The needle drive wire which will pass through the drive wire channels of the angling link and bending links can be coupled to the needle near or inside of the needle tube that will be coupled to the end link 74.

FIGS. 7A, 7B, 7C, 7D, 7E, and 7F are distal, right, left, proximal, top, and bottom elevational views, respectively, of the end link 72. The distal view of FIG. 7A and the proximal view of FIG. 7D show articulation cable attachment slots 108A and 108B where first and second articulation cables 68A and 68B are respectively attached to the end link 72.

FIGS. 8A-8C schematically illustrate how the angler knob 52 is used to adjust a first angle of the flexible span 48 (and therefore the distal tip) with respect to the device shaft 46. For simplicity, only the angling link 70 of the flexible span 48 is shown in FIGS. 8A-8C. The angler drive wire receiver 84 of the angling link 70 is coupled to an angler drive screw 110 by an angler drive wire 112. The inside of the angler knob 52 is in threaded engagement with the angler drive screw 110. The angler drive screw 110 is also able to slide axially with regard to the shaft 46 when moved by rotation of the angler knob 52. In the nominal position of FIG. 8A, the angler drive screw 110 is positioned so that the angler drive wire 112 has the angler link 70 (representative of the flexible span 48) in line with the axis 114 of the shaft 46. As illustrated in FIG. 8B, the angler knob 52 has been rotated around the shaft 46 in a first direction, causing the angler drive screw 110 to move in a proximal direction 116. This causes the angler drive wire 112 to pull on the angler drive wire receiver 84 of the angler link 70, thereby causing the angler link 70 to pivot on the angling hinge pin 76 to create an upward angle $\theta$. As illustrated in FIG. 8C, the angler knob 52 has been rotated around the shaft 46 in a second direction, opposite the first direction, causing the angler drive screw 110 to move in a distal direction 118. This causes the angler drive wire 112 to push on the angler drive wire receiver 84 of the angler link 70, thereby causing the angler link 70 to pivot on the angling hinge pin 76 to create a downward angle β. Depending on the embodiment, the maximum upward angle θ and the maximum downward angle β do not necessarily have to be equal.

Figure 9A:
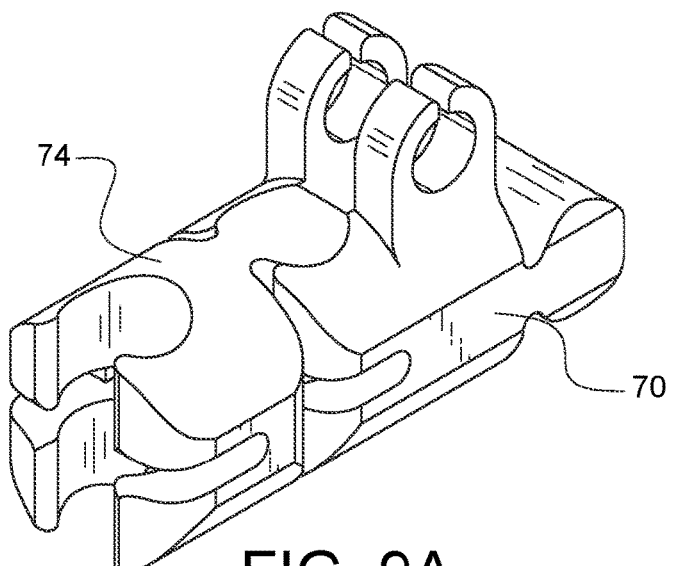
FIG. 9A illustrates how an angling link may be pivotably coupled to a bending link.
Figure 9B:
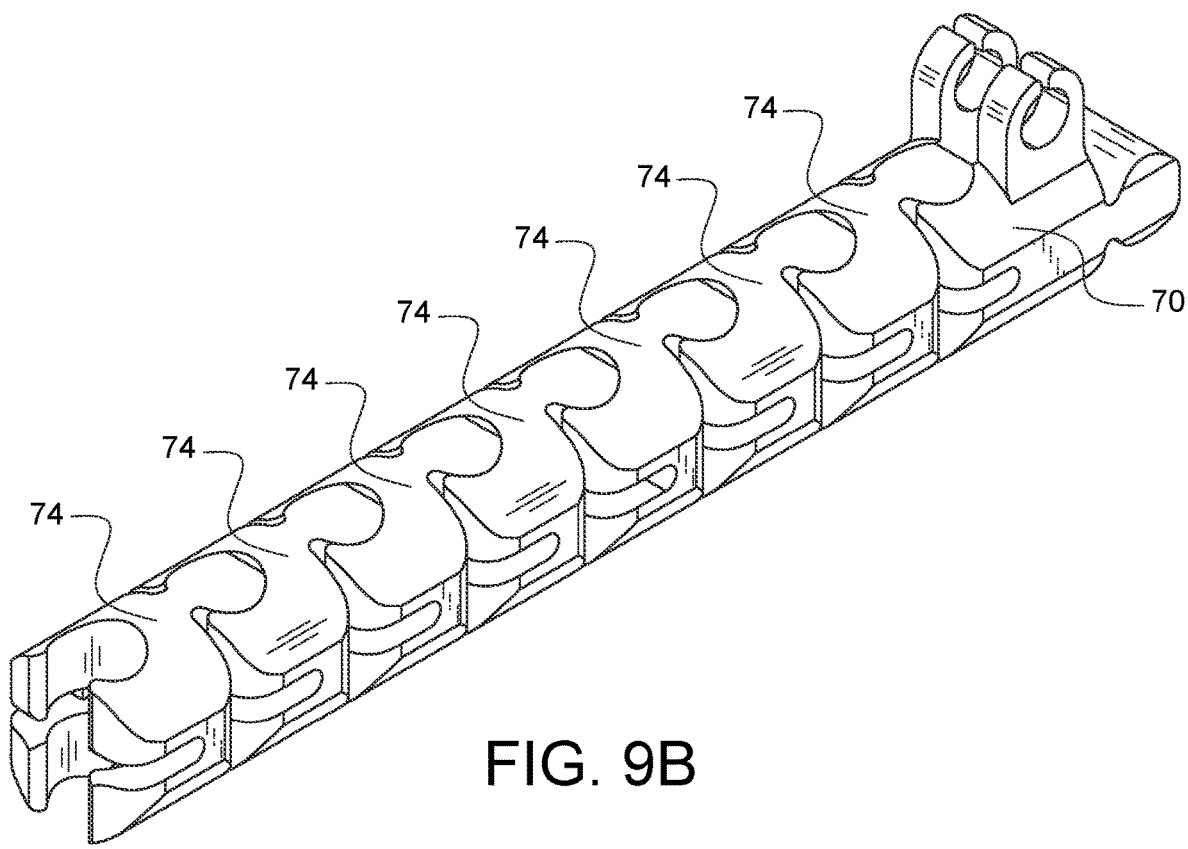
FIG. 9B illustrates how a series of bending links may each be successively pivotably coupled to the next bending link and then the last bending link pivotably coupled to an angling link.
Figure 9C:
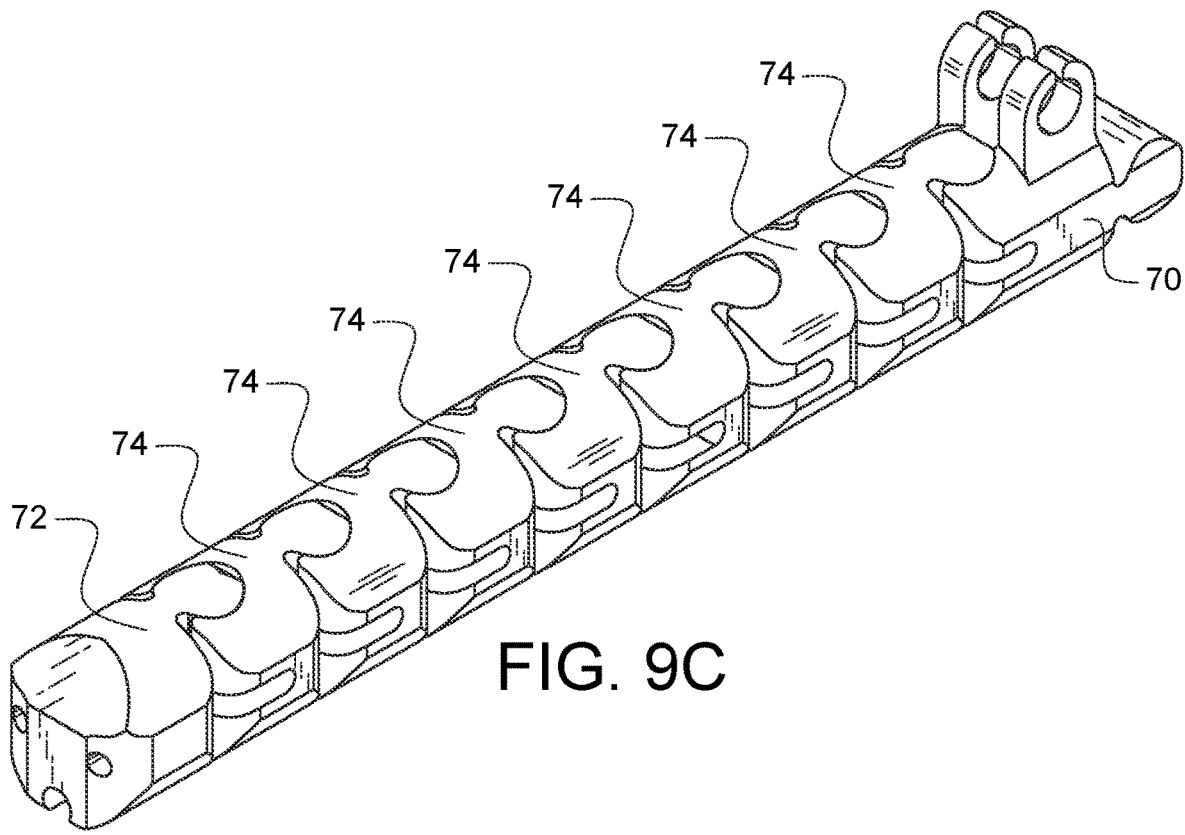
FIG. 9C illustrates the assembly of FIG. 9B with an end link pivotably attached to the distal bending link.

FIG. 9A illustrates how an angling link 70 may be pivotably coupled to a bending link 74. FIG. 9B illustrates how a series of bending links 74 may each be successively pivotably coupled to the next bending link and then the last bending link 74 pivotably coupled to an angling link 70. FIG. 9C illustrates the assembly of FIG. 9B with an end link 72 pivotably attached to the distal bending link 74.

Figure 10:
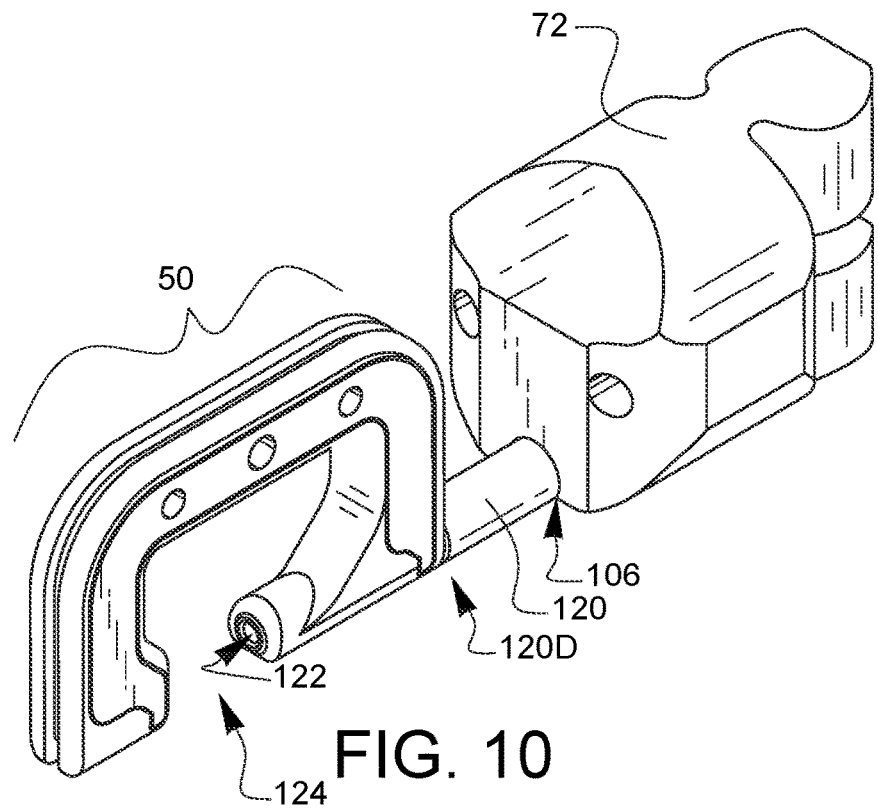
FIG. 10 illustrates how a needle tube can be coupled into a tube receiving slot of an end link.

FIG. 10 illustrates how a needle tube 120 can be coupled into the tube receiving slot 106 of an end link 72. The distal end 120D of the needle tube 120 is coupled to the distal tip 50. The distal tip 50 has a needle channel (not visible in this view) that has an opening 122 from which a needle may be actuated by squeezing the lever 56 discussed above. The distal tip 50 also defines a tissue bite area 124 which will be discussed in more detail further in this specification.

Figure 11:
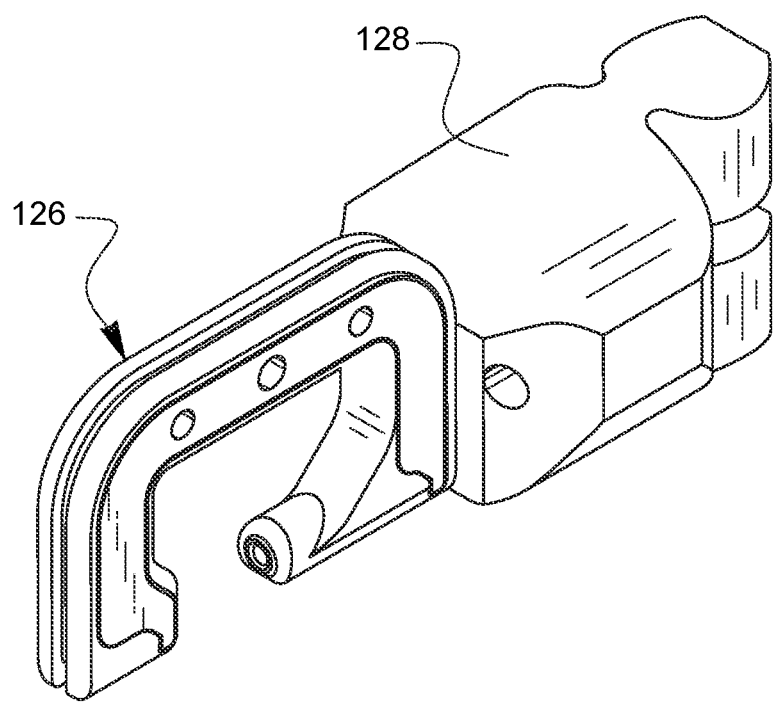
FIG. 11 illustrates another embodiment of a distal tip and end link.

FIG. 11 illustrates another embodiment of a distal tip 126 and end link 128. In the embodiment of FIG. 11, the needle tube may either be fully enclosed within the distal tip 126 and the end link 128, or there may be no need for a needle tube, as the needle channel of the distal tip 126 and a corresponding, aligned channel in the end link 128 may be suitable to guide a needle. The embodiment of FIG. 11 will not be used elsewhere in this specification. Instead, the configurations discussed going forward will have the distal tip 50 and end link 72 shown in FIG. 10.

Figure 12A:
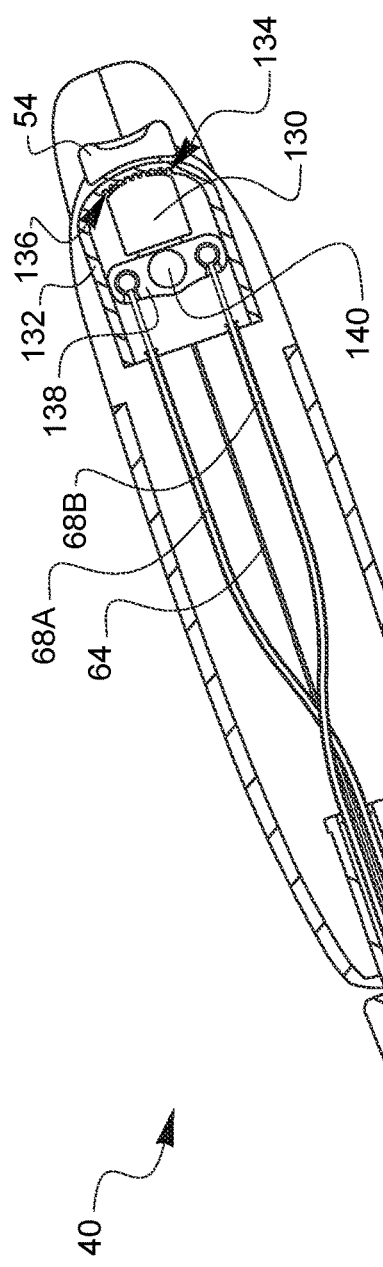
Figure 12B:
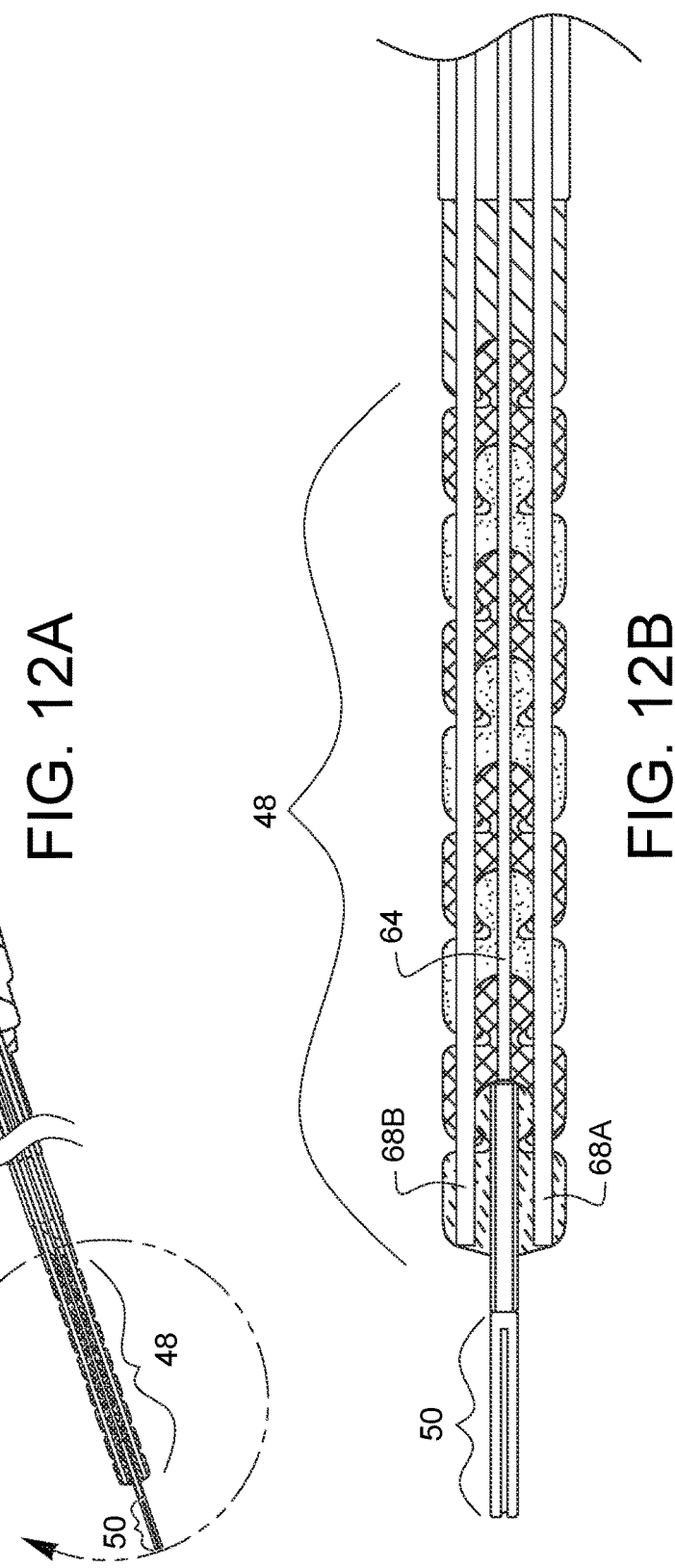
FIG. 12B is an enlarged view of the flexible span from FIG. 12A.

FIGS. 12A, 13A, and 14A are cross-sectioned top schematic views of the minimally invasive suturing device 40 for explaining how the articulation control 54 is used to adjust an articulation angle (a second, separate angle from that discussed with respect to FIGS. 8A-8C). The articulation control 54 is coupled to an indexable block 130 inside of a drive cover 132. The indexable block 130 has indexing teeth 134 which normally engage corresponding teeth 136 on the inside of the drive cover 132. The indexable block 130 is also connected to a yoke 138 which is pivotably coupled to the housing 132 around pivot axis 140. The first and second articulation cables 68A, 68B are each coupled to a different side of the yoke 138. FIG. 12B is an enlarged view of the flexible span 48 from FIG. 12A. When the articulation control is centered as shown in the nominal position of FIG. 12A, the articulation drive cables 68A and 68B are balanced relative to the distal tip 50. This causes the flexible span 48 to be straight as illustrated in FIG. 12B.

The articulation control 54 may be pressed down (into the page in the views of FIGS. 12A, 13A, and 13B) so that the teeth 134 of the indexable block 130 disengage from the corresponding teeth 136 of the drive cover 132. With the teeth 134, 136 disengaged, the articulation control 54 may be pushed to the right 142 as illustrated in FIG. 13A. When the articulation control 54 is released upwards, the teeth 134, 136 will re-engage, holding the articulation control 54 in this rightward position. As shown in FIG. 13A, this rightward movement of articulation control 54 has pivoted the yoke 138 in such a way that the second articulation cable 68B is pulled proximally while the first articulation cable 68A is pushed distally. Since the articulation cables 68A, 68B are crossed in this embodiment, this results in the flexible span 48 being articulated to the right as shown in FIG. 13A and the enlarged view of FIG. 13B.

Alternately, the articulation control 54 may be pressed down and to the left 144 as illustrated in FIG. 14A. When the articulation control 54 is released upwards, the teeth 134, 136 will re-engage, holding the articulation control 54 in this leftward position. As shown in FIG. 14A, this leftward movement of articulation control 54 has pivoted the yoke 138 in such a way that the first articulation cable 68A is pulled proximally while the second articulation cable 68B is pushed distally. Since the articulation cables 68A, 68B are crossed in this embodiment, this results in the flexible span 48 being articulated to the left as shown in FIG. 14A and the enlarged view of FIG. 14B.

Figure 15A:
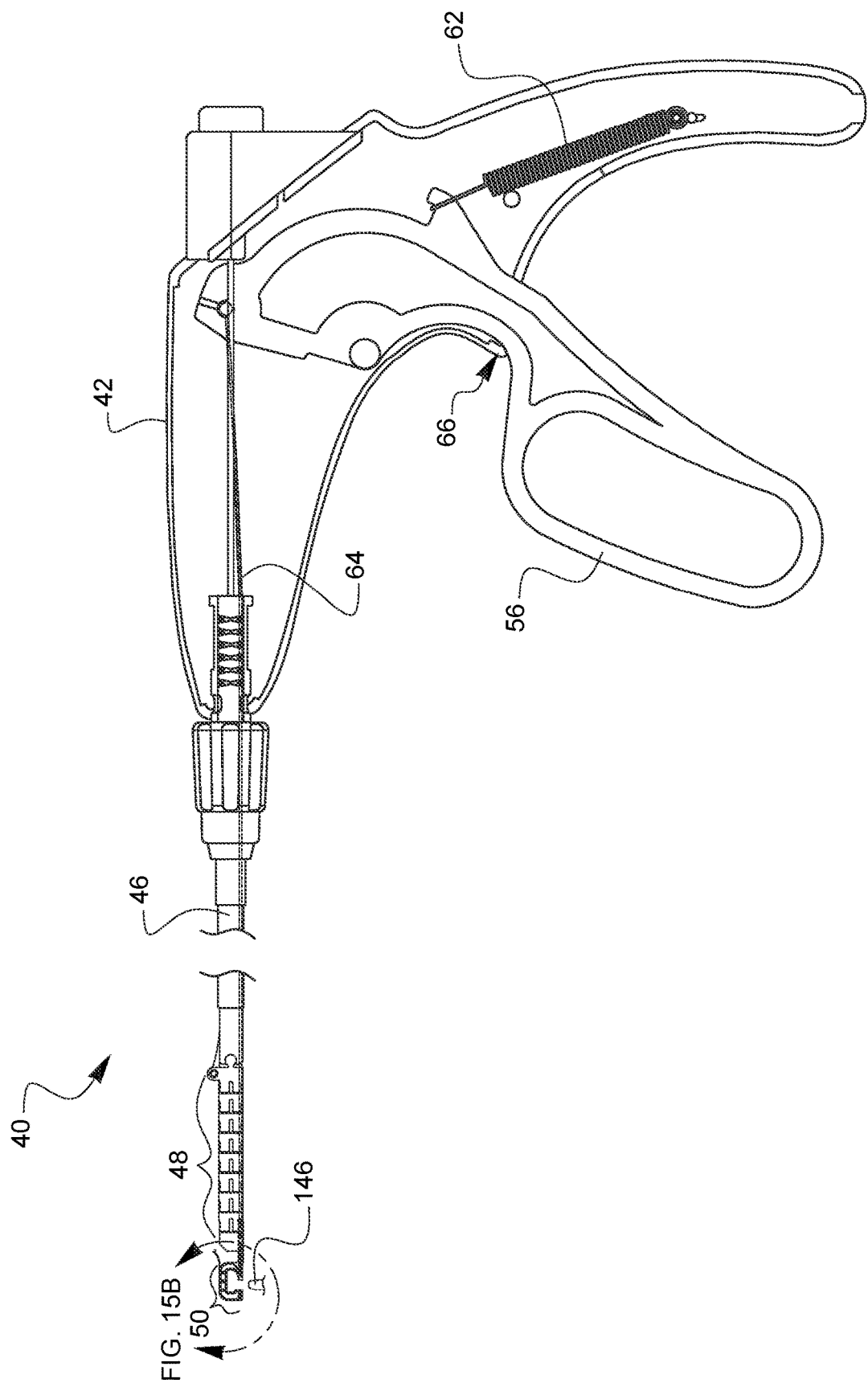
FIG. 15A illustrates a side, partially exposed view of a minimally invasive suturing device in a schematic surgical situation where it is desired to place a suture stitch through a tissue.
Figure 15B:
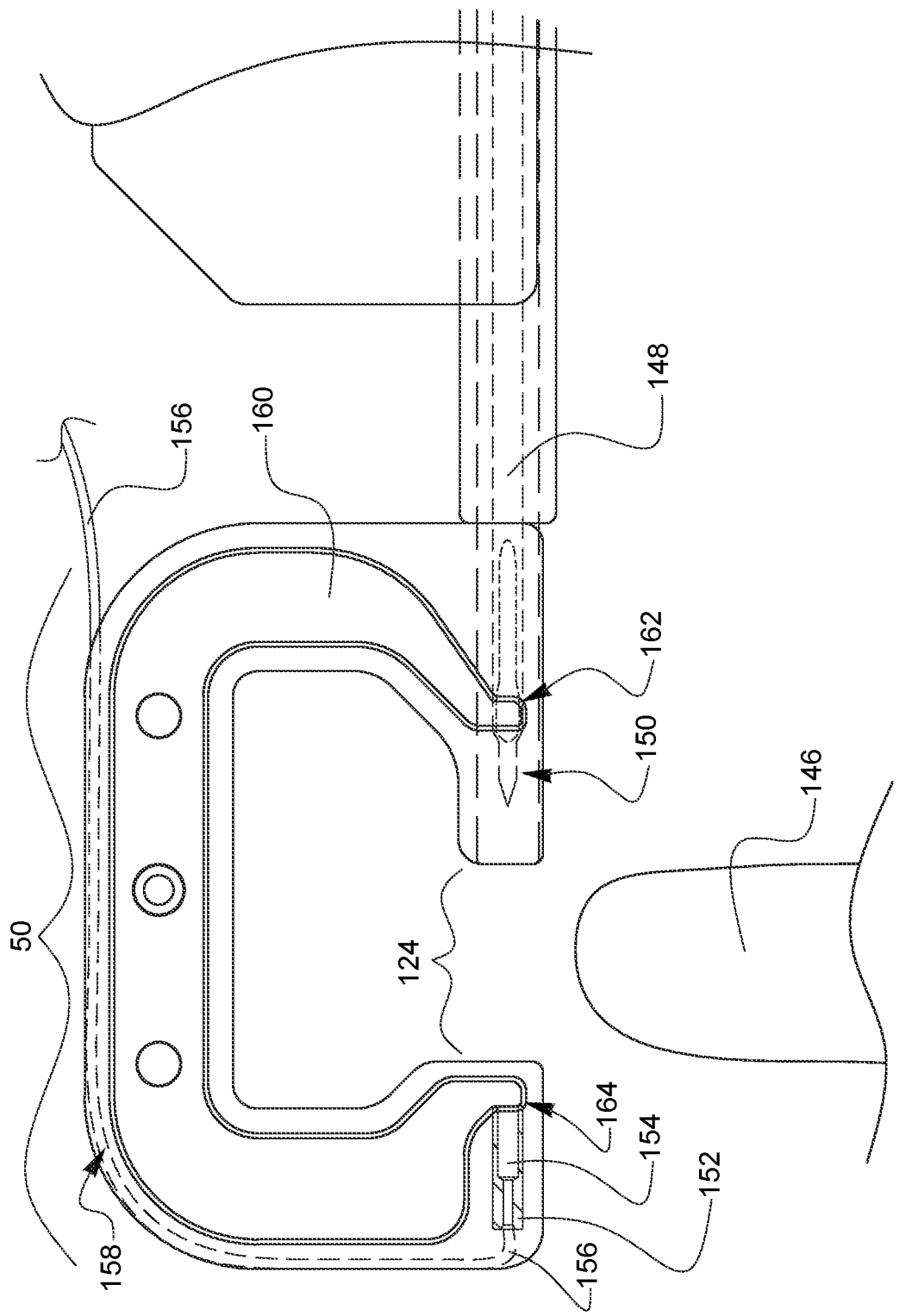
FIG. 15B is an enlarged view of the distal tip and the tissue from FIG. 15A.

FIG. 15A illustrates a side, partially exposed view of the minimally invasive suturing device 40 in a schematic surgical situation where it is desired to place a suture stitch through a tissue 146. In the view of FIG. 15A, the lever 56 is resting against the housing 42 at point 66 due to the biasing force of spring 62. The lever 56 is coupled to a needle drive wire 64 which passes through the shaft 46, through the flexible span 48, and ends in a needle 148 which is visible in FIG. 15B, an enlarged view of the distal tip 50 and the tissue 146 from FIG. 15A. The needle 148 has a ferrule engaging tip 150 which is currently housed within the distal tip 50. The distal tip 50 has a tissue bite area 124 which was discussed previously. A ferrule holder 152 is located distally across the tissue bite area 124 from the ferrule engaging tip 150 of the needle 148. A ferrule 154 is attached to one end of a suture 156. The ferrule 154 has been loaded into the ferrule holder 152, and the suture 156 has been routed in a suture channel 158 which runs around the outside of the distal tip 50. A double-ended spring 160 has a first end 162 which rides on the needle 148 on the proximal side of the tissue bite area 124. The double-ended spring 160 also has a second end 164 which is positioned to ride on the needle 148 when it is engaged to cross the tissue bite area 124 as will be discussed in more detail below. The second end 164 can also help to retain the ferrule 154 in the ferrule holder 152.

Figure 16A:
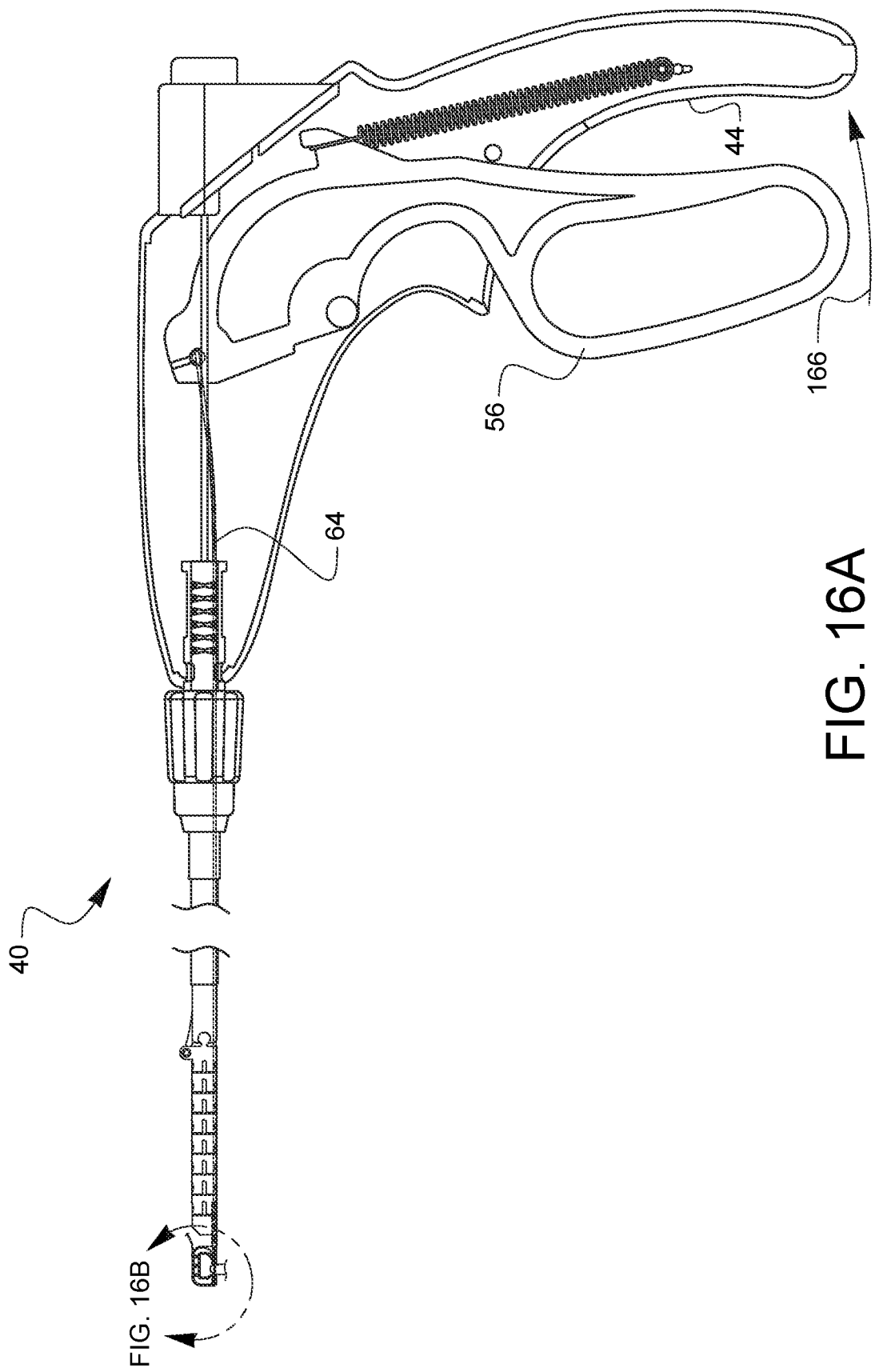
FIG. 16A and the corresponding enlarged view of FIG. 16B show the device positioned so that the tissue bite area is over the tissue.
Figure 16B:
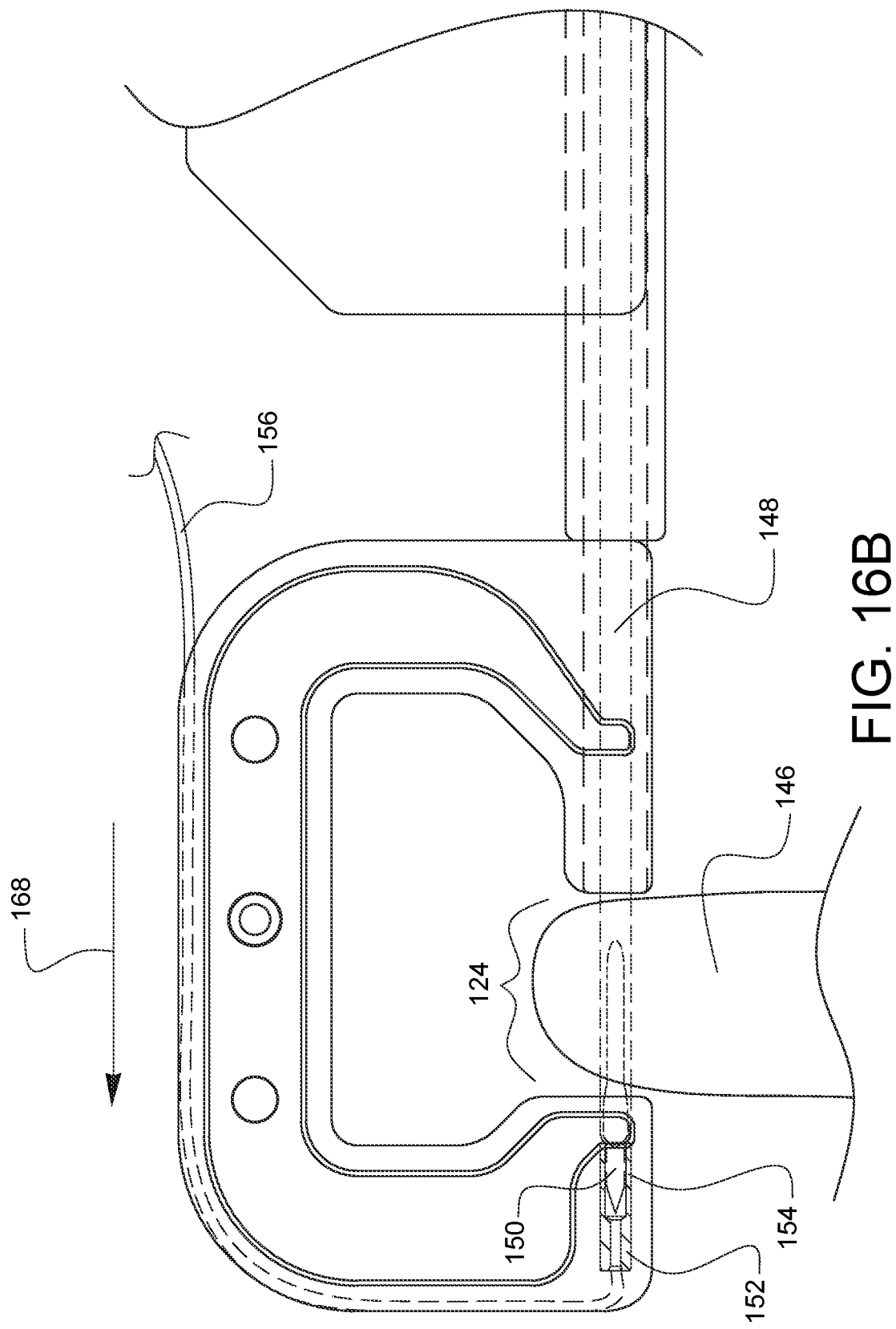

As illustrated in FIG. 16A and the corresponding enlarged view of FIG. 16B, the device 40 is positioned so that the tissue bite area 124 is over the tissue 146. The lever 56 is squeezed 166 towards the handle 44 causing the needle drive wire 64 to move distally 168. As can be seen more clearly in FIG. 16B, this causes the needle 148 to move distally through the tissue 146 and into contact with the ferrule 154. The ferrule engaging tip 150 is sized to have an interference fit with the inside of the ferrule 154, and thus the ferrule engaging tip 150 and the ferrule 154 are coupled together.

Figure 17A:
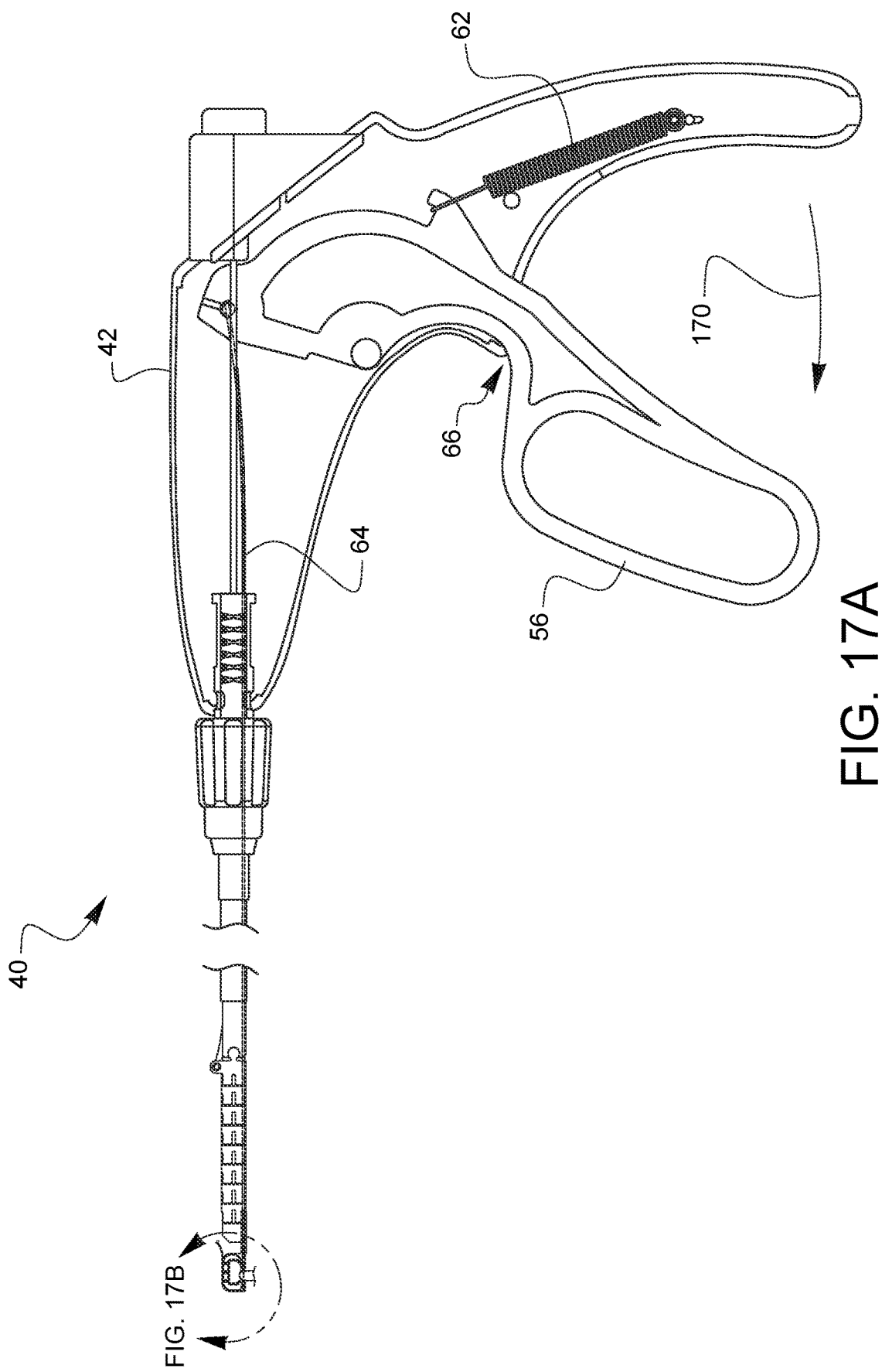
FIG. 17A and the corresponding enlarged view of FIG. 17B show an embodiment where the handle is released and the spring causes the lever to return into contact with the housing.
Figure 17B:
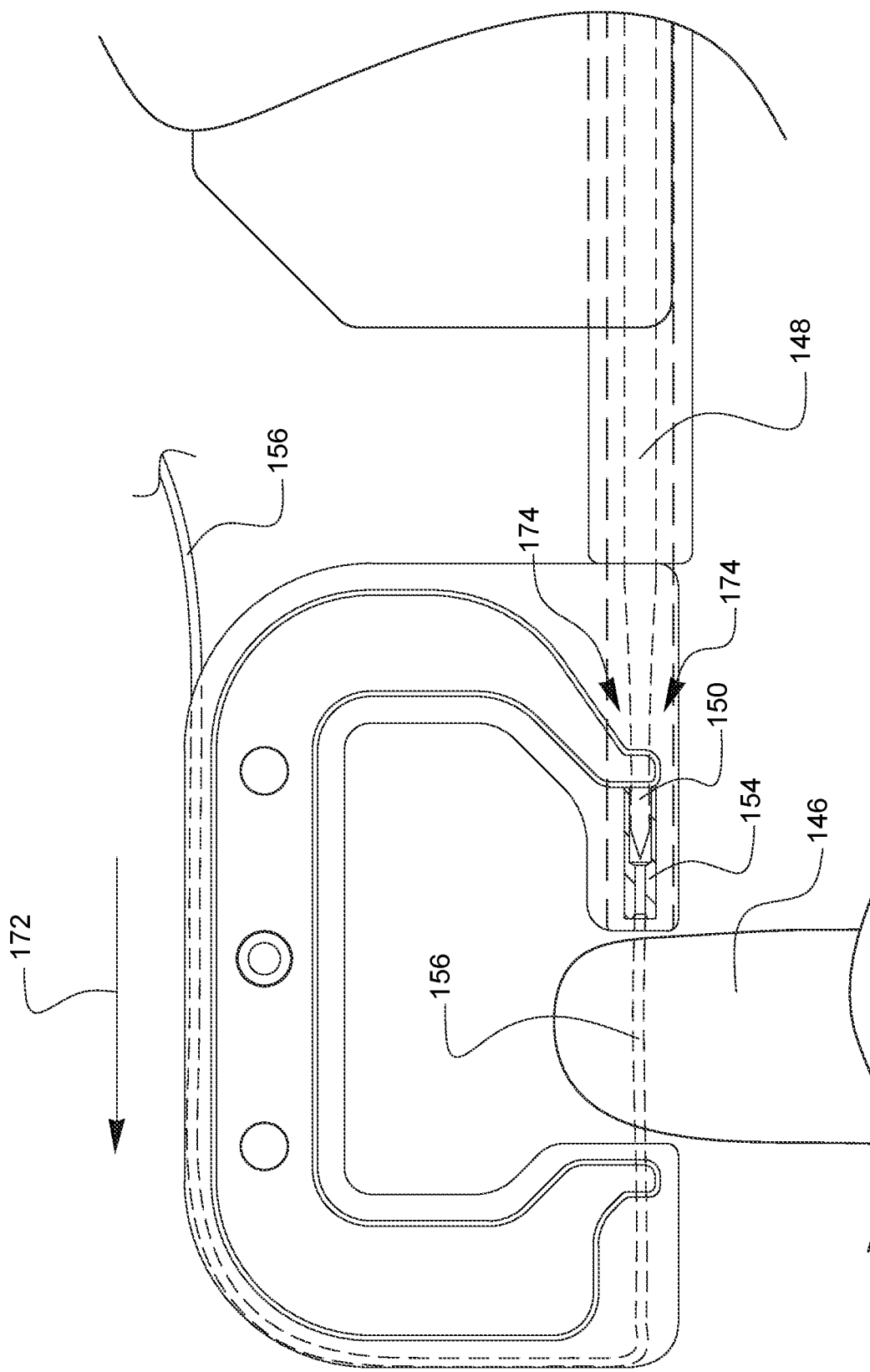

As illustrated in FIG. 17A and the corresponding enlarged view of FIG. 17B, the handle 56 is released 170 and the spring 62 causes the lever 56 to return into contact with the housing 42 at point 66. This movement of the lever 56 causes the needle 148 to retract in a proximal direction 172, pulling the attached ferrule 154 and its suture 156 back through the tissue 146. In some embodiments, the proximal movement 172 of the needle 148 can also be combined with a ninety degree rotation of the needle on its own needle axis as shown in FIG. 17B. As rotated, one of the ramps 174 is now oriented so that it can be contacted by the second end 164 of the double-ended spring 160 in a subsequent step. Those skilled in the art are familiar with ways to cause this ninety degree rotation of the needle 148.

Figure 18A:
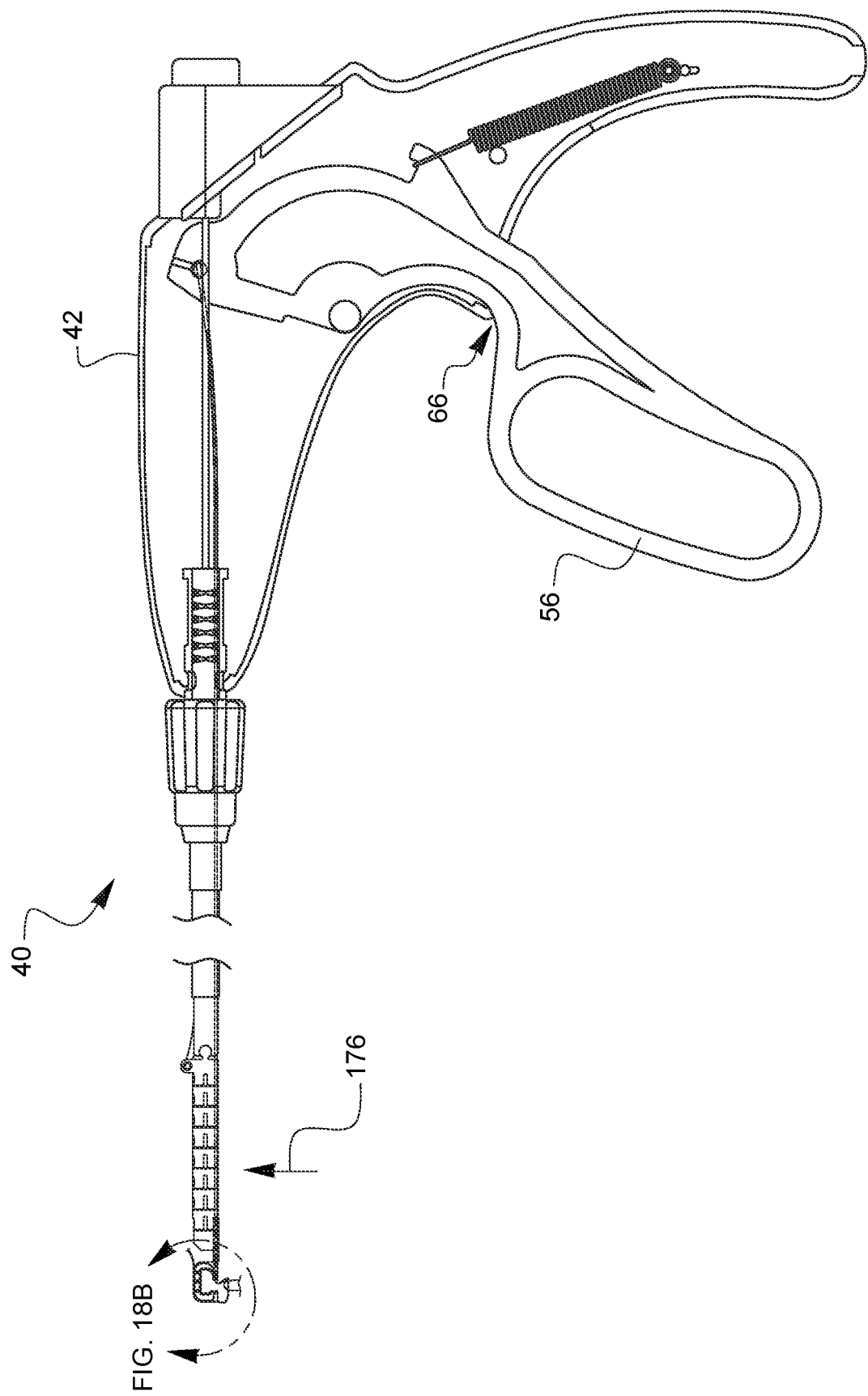
FIG. 18A and the corresponding enlarged view of FIG. 18B show an embodiment where the device is then lifted off of the tissue.
Figure 18B:
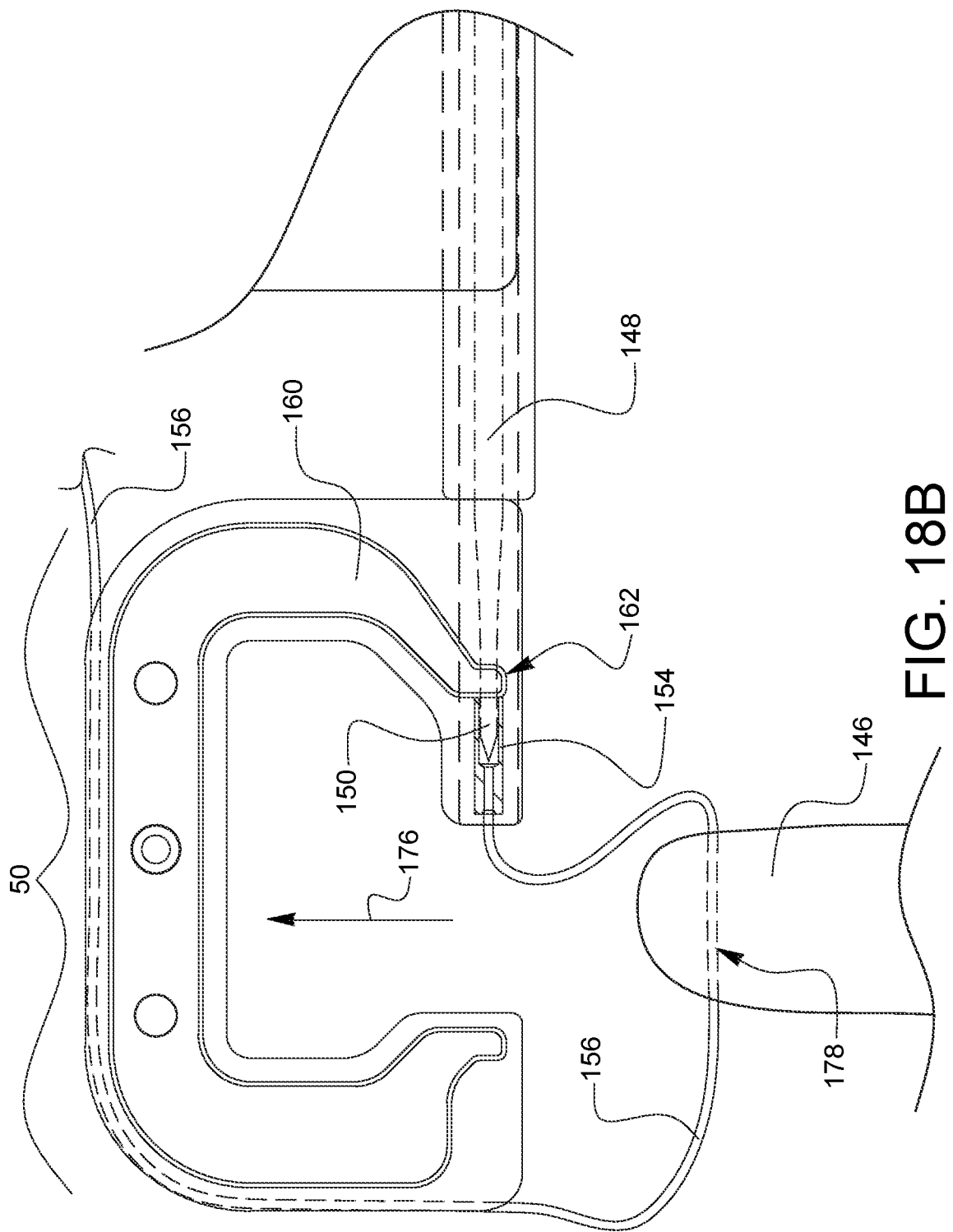

As illustrated in FIG. 18A and the corresponding enlarged view of FIG. 18B, the device 40 is then lifted 176 off of the tissue 146. The first suture stitch 178 of the suture 156 through the tissue 146 remains.

Figures 19A, 19B:
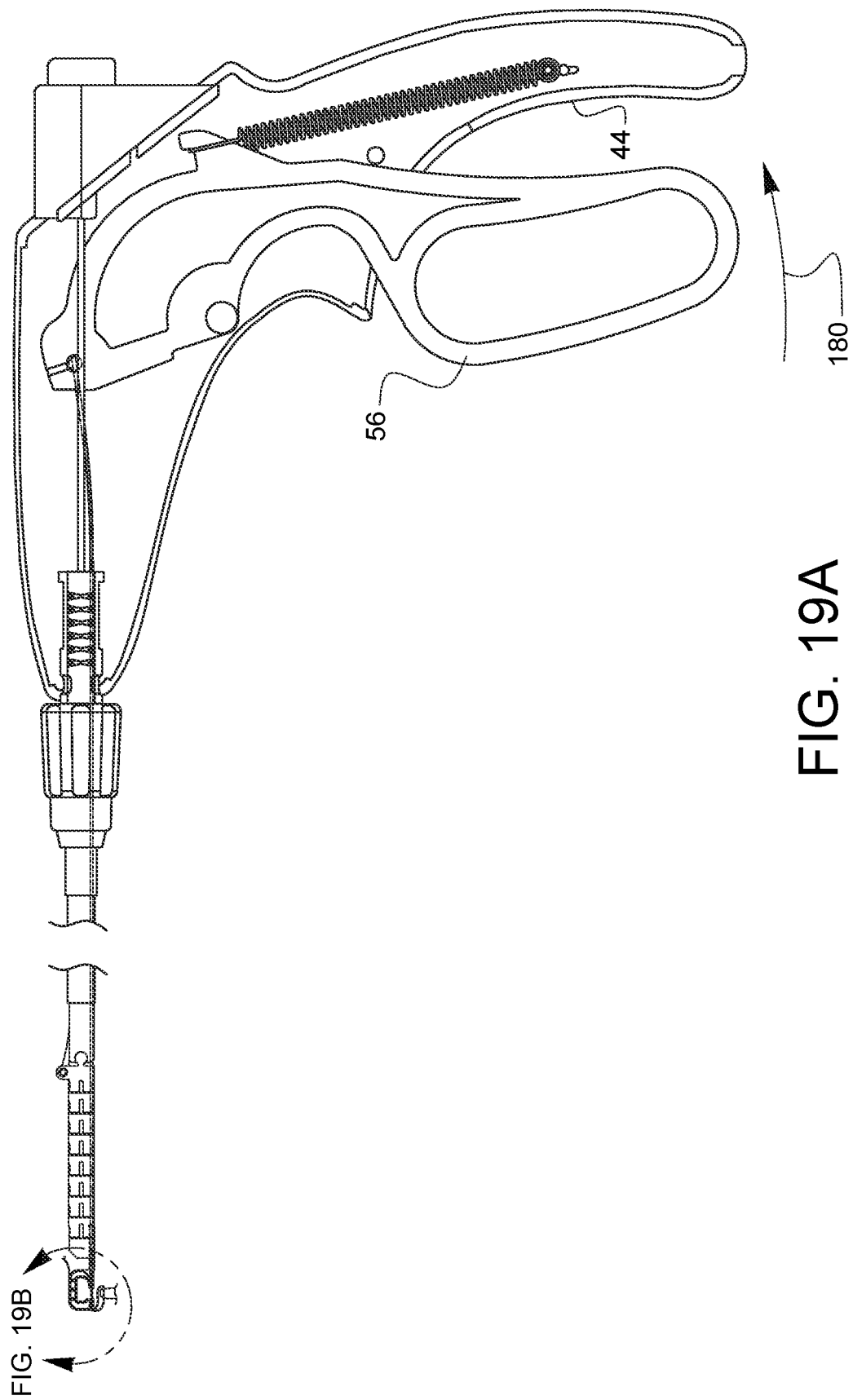
FIG. 19A and the corresponding enlarged view of FIG. 19B show an embodiment where, while the device's tissue bite area is clear of tissue, the lever is squeezed towards the handle, causing the needle to move distally across the tissue bite area, returning the ferrule to its ferrule holder.
Figure 19B:
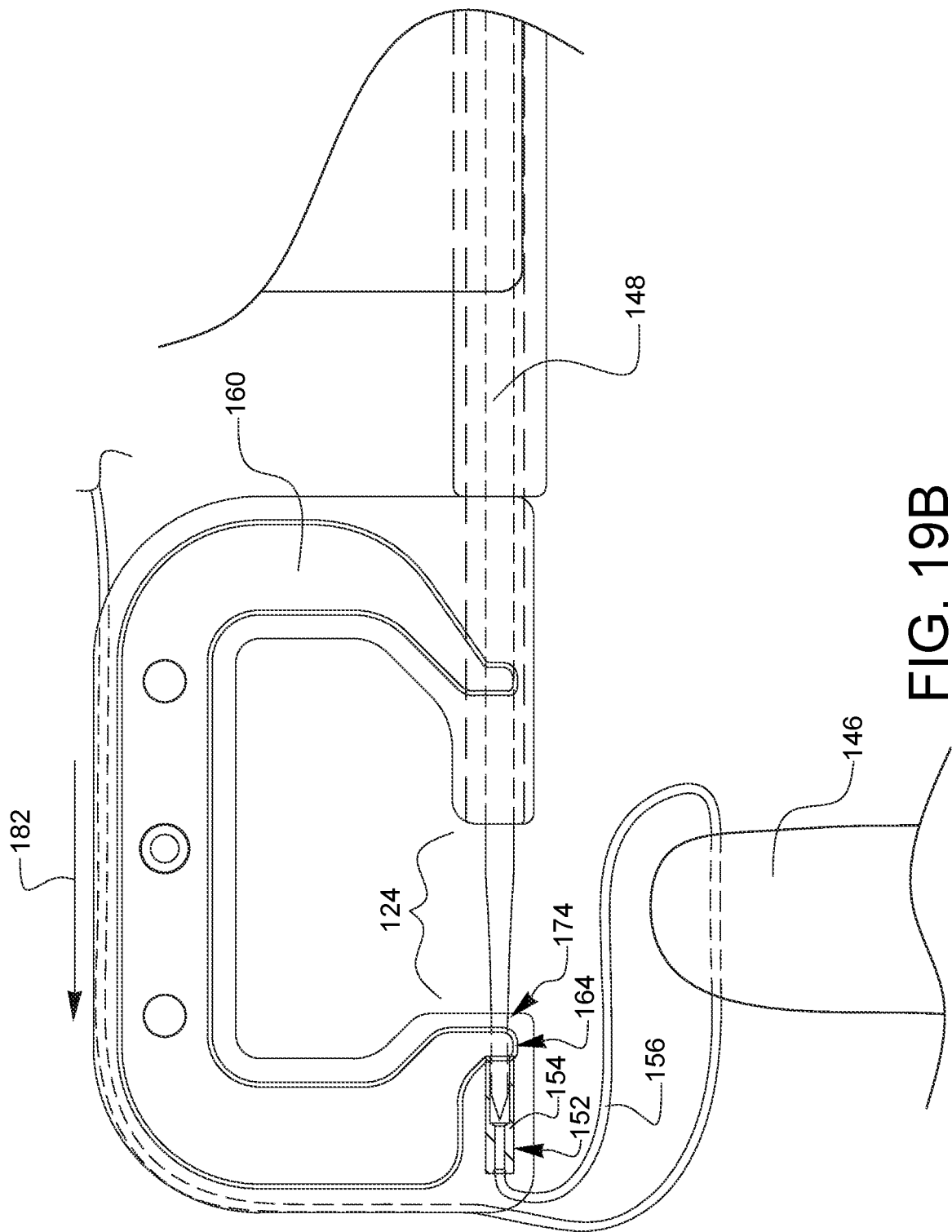

As illustrated in FIG. 19A and the corresponding enlarged view of FIG. 19B, while the device's tissue bite area 124 is clear of tissue, the lever 56 is squeezed 180 towards the handle 44, causing the needle 148 to move distally 182 across the tissue bite area 124, returning the ferrule 154 to its ferrule holder 152. The second end 164 of the double-ended spring 160 rides onto the ramp 174 of the needle 148 just past the ferrule 154.

Figure 20A:
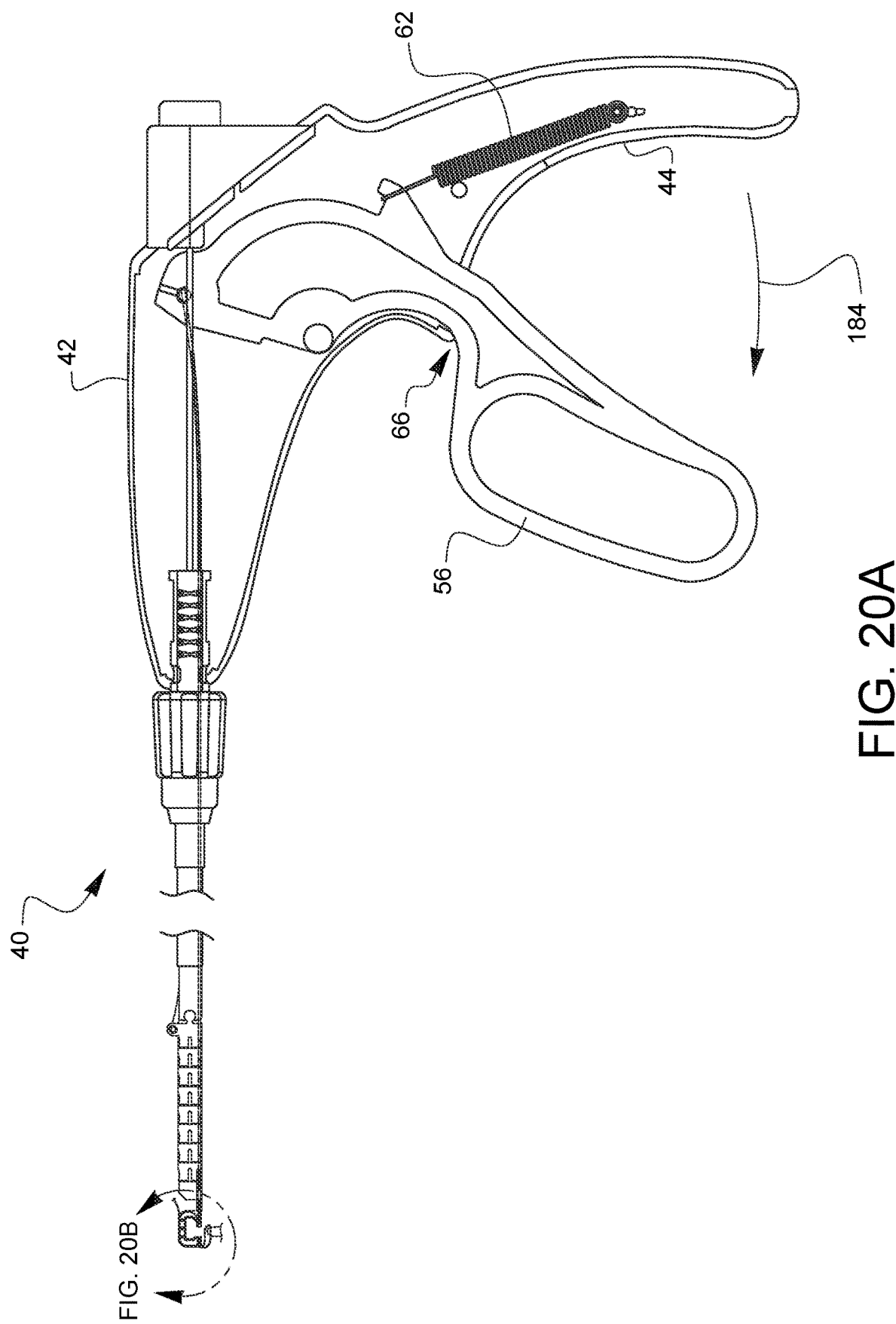
FIG. 20A and the corresponding enlarged view of FIG. 20B show an embodiment where the lever is released, allowing the spring to move the lever back into contact with the housing at point.

As illustrated in FIG. 20A and the corresponding enlarged view of FIG. 20B, the lever is released, allowing the spring 62 to move 184 the lever 56 back into contact with the housing 42 at point 66. This retracts the needle 148 back across the tissue bite area 124, however, because the second end 164 of the double-ended spring 160 was riding on the ramp 174 of the needle 148 as shown in FIG. 19B, when the needle 148 retracts as shown in FIG. 20B, the second end 164 of the double-ended spring 160 pulls the ferrule 154 off of the needle tip 150, retaining it in the ferrule holder 152. As before, using mechanisms known to those skilled in the art, the needle 148 is rotated another ninety degrees around the needle's axis while the needle 148 is retracted. The suturing device 40 is now reset to the state of FIGS. 15A and 15B and is ready to make another stitch in the tissue 146.

When the desired number of stitches have been made, the device may be pulled off of the tissue as was shown in FIG. 18B. The ferrule 154 can be removed from the needle 148 and the distal tip 50 by hyper-extending the lever 56 against the housing 42 at point 66. This will cause the needle 148 to move from the position shown in FIG. 18B in a proximal direction so that the ferrule 154 is removed from the needle tip 150 by the first end 162 of the double-ended spring 160.

Various advantages of a minimally invasive suturing device have been discussed above. Embodiments discussed herein have been described by way of example in this specification. It will be apparent to those skilled in the art that the forgoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A minimally invasive surgical device, comprising:
   a housing;
   an actuator coupled to a first portion of the housing;
   a shaft coupled to a second portion of the housing, the shaft extending from a proximal end to a distal end about a shaft axis, and wherein one or more interior surfaces of the shaft defines a shaft interior portion, and wherein a shaft mating feature is disposed at the distal end of the shaft;
   a needle coupled to the actuator such that the needle is displaceable from a first position to a second position, wherein the needle comprises a needle tip at a distal end of the needle, and wherein at least a portion of the needle is disposed within the shaft interior portion;
   an elongated flexible span extending from a proximal end to a distal end about a span axis, wherein the proximal end of the flexible span is disposed at or adjacent to the distal end of the shaft, the flexible span comprising:
   an angling link disposed at the proximal end of the flexible span, the angling link comprising:
   an angling link body;
   a first angling link mating feature disposed at a proximal end of the angling link body and extending along a first pivot axis; and
   a second angling link mating feature disposed at a distal end of the angling link body and extending along a second pivot axis that is normal to the first pivot axis;
   a plurality of bending links, wherein each of the plurality of bending links comprises:
   a bending link body;
   a first bending link mating feature disposed at a proximal end of the bending link body; and
   a second bending link mating feature disposed at a distal end of the bending link body, wherein each of the plurality of bending links includes only one first bending link mating feature and only one second bending link mating feature; and
   an end link disposed at the distal end of the flexible span, the end link comprising:
   an end link body; and
   a first end link mating feature disposed at a proximal end of the end link body and extending along a third pivot axis that is parallel to the second pivot axis,
   wherein the first angling link mating feature of the angling link engages the shaft mating feature such that the flexible span rotates relative to the distal end of the shaft about the first pivot axis,
   wherein the plurality of bending links are aligned such a first of the plurality of bending links is disposed adjacent to the distal end of the angling link body and a second of the plurality of bending links is disposed adjacent to the proximal end of the end link body,
   wherein the first bending link mating feature of the first of the plurality of bending links engages the second angling link mating feature of the angling link such that the first of the plurality of bending links rotates relative to the angling link about the second pivot axis that is normal to the first pivot axis,
   wherein the second bending link mating feature of the second of the plurality of bending links engages the first end link mating feature of the end link such that the second of the plurality of bending links rotates relative to the end link about the third pivot axis that is parallel to the second pivot axis,
   and wherein the first bending link mating feature of each of the plurality of bending links between the first of the plurality of bending links and the second of the plurality of bending links engages the second bending link mating feature of an adjacent one of the bending links between the first of the plurality of bending links and the second of the plurality of bending links such that each of the plurality of bending links is pivotable relative to the adjacent one of the bending links about a pivot axis that is parallel to the second pivot axis and the third pivot axis,
   and wherein the first bending link mating feature of each of the plurality of bending links between the first of the plurality of bending links and the second of the plurality of bending links is one of a cylindrical or partially-cylindrical protrusion or a cylindrical or partially-cylindrical socket, and the second bending link mating feature of the adjacent one of the bending links is the other of the cylindrical or partially-cylindrical protrusion or the cylindrical or partially-cylindrical socket such that the cylindrical or partially-cylindrical protrusion is received into the cylindrical or partially-cylindrical socket such that the cylindrical or partially-cylindrical protrusion rotates within the cylindrical or partially-cylindrical socket; and a distal tip coupled to the end link of the flexible span, wherein a notch in the distal tip defines a tissue bite area configured to receive a portion of tissue, wherein when the needle is in the first position, the needle tip of the needle is disposed at a proximal portion of the tissue bite area and when the needle is in the second position, the needle tip of the needle is disposed at a distal portion of the tissue bite area such that the needle tip of the needle extends through the portion of tissue disposed in the tissue bite area.

2. The minimally invasive surgical device of claim 1, further comprising:
an articulation control; and
first and second articulation cables which pass through articulation cable channels in the angling link and the plurality of bending links to be attached to different sides of the end link.

3. The minimally invasive surgical device of claim 1, further comprising a needle drive wire which passes through a drive wire channel in each of the angling link and the plurality of bending links to couple with a portion of the needle disposed in a needle guide tube held by the end link.

4. The minimally invasive surgical device of claim 3, wherein the distal tip is coupled to the needle guide tube.

5. The minimally invasive surgical device of claim 1, wherein an articulation socket defines a bending axis.

6. The minimally invasive surgical device of claim 1, further comprising an angler knob coupled to one or more portions of the flexible span, wherein:
rotating the angler knob in a first direction causes the flexible span to displace in a first direction relative to the shaft; and
rotating the angler knob in a second direction causes the flexible span to displace in a second direction relative to the shaft.

7. The minimally invasive surgical device of claim 1, wherein the shaft mating feature has a cylindrical or partially-cylindrical shape and the first angling link mating feature has a corresponding cylindrical or partially-cylindrical shape, and the first pivot axis is coaxially aligned with the corresponding cylindrical or partially-cylindrical shape of the first angling link mating feature.

8. The minimally invasive surgical device of claim 7, wherein the shaft mating feature is a cylindrical or partially-cylindrical slot and the first angling link mating feature is a corresponding cylindrical or partially-cylindrical angling hinge pin received in the slot, and the first pivot axis is coaxially aligned with the angling hinge pin.

9. The minimally invasive surgical device of claim 8, wherein the second angling link mating feature is a cylindrical or partially-cylindrical articulation socket and the first bending link mating feature is a corresponding cylindrical or partially-cylindrical bending hinge pin received in the articulation socket, and the second pivot axis is coaxially aligned with the articulation socket.

10. The minimally invasive surgical device of claim 9, wherein the first end link mating feature is a cylindrical or partially-cylindrical end link hinge pin and the second bending link mating feature is a corresponding cylindrical or partially-cylindrical bending socket that receives the end link hinge pin, and the third pivot axis is coaxially aligned with the end link hinge pin.

11. The minimally invasive surgical device of claim 1, wherein the cylindrical or partially-cylindrical socket extends from a first point at or adjacent to a top surface of the bending link body to a second point at or adjacent to a bottom surface of the bending link body that is opposite the top surface of the bending link body.

12. The minimally invasive surgical device of claim 1, wherein the first pivot axis is normal to the shaft axis.

* * * * *